United States Patent [19]

Myers

[11] Patent Number: 5,352,719

[45] Date of Patent: Oct. 4, 1994

[54] HINDERED AMINE LIGHT STABILIZER HYDRAZIDES

[75] Inventor: Terry N. Myers, Erie, N.Y.

[73] Assignee: Elf Atochem North America, Inc., Philadelphia, Pa.

[21] Appl. No.: 849,904

[22] Filed: Mar. 12, 1992

Related U.S. Application Data

[62] Division of Ser. No. 553,923, Jul. 17, 1990, Pat. No. 5,116,976.

[51] Int. Cl.⁵ .......................................... C08K 5/3435
[52] U.S. Cl. ...................................... 524/102; 524/97; 524/99; 524/103; 524/291
[58] Field of Search ................... 524/97, 99, 102, 103, 524/291

[56] References Cited

U.S. PATENT DOCUMENTS

| | | | |
|---|---|---|---|
| 3,639,334 | 2/1972 | Holoch | 260/45.9 |
| 3,941,744 | 3/1976 | Murayama et al. | 260/45.8 |
| 3,975,462 | 8/1976 | Murayama et al. | 260/880 |
| 4,005,094 | 1/1977 | Murayama et al. | 293/66 |
| 4,145,512 | 3/1979 | Uhrhan et al. | 528/73 |
| 4,153,596 | 5/1979 | Oertel et al. | 260/45.8 |
| 4,178,279 | 12/1979 | Uhrhan et al. | 260/45.8 |
| 4,223,147 | 9/1980 | Oertel et al. | 546/224 |
| 4,241,208 | 12/1980 | Murayama et al. | 546/20 |
| 4,247,449 | 1/1981 | Wiezer et al. | 260/45.8 |
| 4,336,183 | 6/1982 | Nakahara et al. | 524/95 |
| 4,396,735 | 8/1983 | Minagawa et al. | 524/92 |
| 4,408,051 | 10/1983 | Hinsken et al. | 546/19 |
| 4,526,966 | 7/1985 | Wiezer | 524/95 |
| 4,562,220 | 12/1985 | Wiezer | 524/95 |
| 4,689,416 | 8/1987 | Ertl et al. | 546/19 |
| 4,745,192 | 5/1988 | Ertl | 546/19 |
| 4,755,602 | 7/1988 | Ertl | 546/19 |
| 4,824,844 | 4/1989 | MacLeay et al. | 524/99 |
| 4,857,595 | 8/1989 | Kazmierzak et al. | 525/142 |

FOREIGN PATENT DOCUMENTS

| | | | |
|---|---|---|---|
| 413402 | 7/1985 | Canada | 546/20 |
| 352367 | 1/1986 | Fed. Rep. of Germany | 546/20 |

OTHER PUBLICATIONS

Encyclopedia of Polymer Science & Engineering, 2nd Ed., vol. 2, pp. 83–84—"Metal Deactivators", (1985).

Chemical Abstracts, vol. 92, 1980, p. 34, 42845j; "Light Stabilizers for Synthetic Resins", Abstracting Japan 79/95649.

Chemical Abstracts, vol. 92, 1980, 59703j, p. 36, "Light Stabilizers for Synthetic Polymers", Abstracting Japan 79/103,461.

*Primary Examiner*—Kriellion S. Morgan
*Attorney, Agent, or Firm*—Stanley A. Marcus; Royal E. Bright

[57] ABSTRACT

New and novel stabilized polymer compositions and processes for preparing them which employ new and novel carboxylic acid hydrazides bearing a 2,2,6,6-tetraalkyl-4-piperidine ring and new and novel polymeric compositions stabilized therewith are provided.

29 Claims, No Drawings

HINDERED AMINE LIGHT STABILIZER HYDRAZIDES

This application is a divisional of application Ser. No. 07/553,923 filed Jul. 17, 1990, now U.S. Pat. No. 5,116,976.

BACKGROUND OF THE INVENTION

1. Field of the Invention

This invention relates to derivatives of N-(2,2,6,6-tetraalkyl-4-piperidinyl)-containing carboxylic acid hydrazides. These compounds are very efficient in the stabilization of polymeric systems which are subject to degradation upon exposure to heat and/or light. These compounds contain both a hindered amine light stabilizing group and an acid hydrazide or derivative thereof. The acid hydrazide derivative enhances the photooxidative stabilizing properties of the hindered amine groups and contributes thermooxidative stabilizing and metal complexing properties to the compounds.

1. Description of the Prior Art

Hindered amine light stabilizers bearing carboxylic acid hydrazide functionality (hereinafter HALS-hydrazides) and derivatives thereof are known. There are five examples in the literature where the hindered amine moiety and the hydrazide moiety (—C(=O)—NH—NH$_2$) are present in the same molecule.

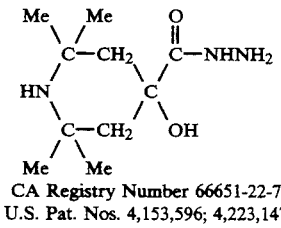

CA Registry Number 66651-22-7
U.S. Pat. Nos. 4,153,596; 4,223,147

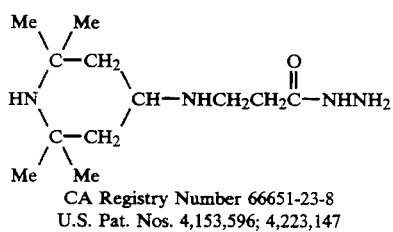

CA Registry Number 66651-23-8
U.S. Pat. Nos. 4,153,596; 4,223,147

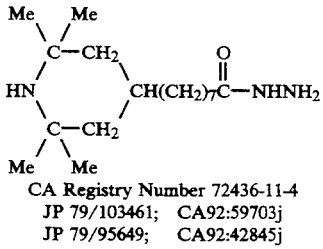

CA Registry Number 72436-11-4
JP 79/103461; CA92:59703j
JP 79/95649; CA92:42845j

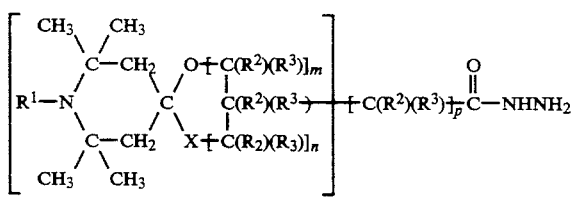

X = O, NH; n = 0, 1, 2; m = 1, 2; p = 0, 1
U.S. Pat. No. 4,336,183; CA97:217369g

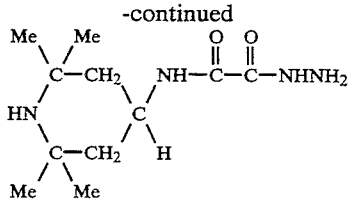

U.S. Pat. application Ser. No. 310,408
filed March 13, 1989, now U.S. Pat. No. 4,983,738.

Derivatives of these HALS-hydrazides are disclosed in several patents. U.S. Pat. Nos. 4,145,512 and 4,178,279 teach the reaction of HALS-hydrazide groups with isocyanate groups of polyisocyanates of isocyanate prepolymers to obtain light stabilized polyurethanes. U.S. Pat. No. 4,336,183 discloses acyl derivatives of HALS-hydrazides. U.S. Pat. No. 4,824,884 discloses cyclic anhydride derivatives of the parent N-(2,2,6,6-tetraalkyl-4-piperidinyl)amic acid hydrazides (of U.S. patent application Ser. No. 310,408). These derivatives are also efficient heat and light stabilizers for polymeric systems but do not fall under the scope of this invention.

U.S. Pat. No. 4,396,735 discloses mixtures of hindered amine light stabilizers and heterocyclic acid hydrazides for stabilizing synthetic resin compositions. Such systems are described as synergistic, since the combination is better than the hindered amine alone, and the hydrazide alone is not a light stabilizer.

In addition to activity as a stabilizer, commercially useful stabilizer additives must have both excellent compatibility with and/or solubility in the polymeric substrates to be stabilized along with superior resistance to loss from the stabilized composition during processing and end-use application. Many stabilizer additives exhibit limited compatibility in certain substrates and excessive tendency to exude, sublime and/or volatilize during weathering or processing of the stabilized composition. A major problem often exists when use conditions require prolonged exposure to elevated temperatures. Therefore, several attempts have been made to increase the compatibility and reduce the volatility of such stabilizer additives in various resin systems by modifying their structures. While improvements have been noted over the years, experience has shown that state-of-the-art stabilizers do not exhibit the desired combination of properties in all resins. Continued evolution of new polymeric compositions guarantees the need for additional structural modifications on any potential heat and/or light stabilizer intended for use. The versatility of the HALS-hydrazides disclosed herein allows for adaptation of the stabilizer combination to suit such new compositions.

The novel HALS-hydrazides of the instant invention are reactive hydrazides, capable of forming typical hydrazide derivatives. They can react with a variety of functional groups to permit property adjustment (such as compatibility and volatility). By careful selection of the proper derivative, one can increase the compatibility of the novel compounds with various host resins to be stabilized. The novel derivatives have low volatility and are not readily lost from polymeric systems via volatilization, migration or extraction. For example they react with cyclic anhydrides with formation of imides or amic acids; esters or acid halides with formation of acyl hydrazides; ketones and aldehydes with formation of hydrazones; chloroformates with formation of semicarbazates; and isocyanates with formation of semicarbazides. The diacyl hydrazide function (formed by reaction of the hydrazide with an anhydride, ester or acid halide) is known to be particularly resistant to thermal degradation and a particularly useful antioxidant function (U.S. Pat. No. 3,639,334).

Polymers such as polyolefins (e.g. polyethylene, polypropylene, etc.) styrenics (e.g. polystyrene, rubber modified polystyrene, ABS, MBS etc.), polyvinyl chloride, polycarbonates, polyesters, polyphenylene ethers and polyamides for example are subject to degradation and discoloration upon exposure to heat and/or light with consequent deterioration of their mechanical properties. Various stabilizers have been proposed to inhibit such deterioration. Hindered piperidine light stabilizers have found extensive use in the photostabilization of polyolefins. Prior to the present invention, the results obtained with the known hindered amine light stabilizers have not been fully satisfactory with all types of manufactured articles, either from a stabilization, compatibility, volatility, extrudability or economic viewpoint or combinations thereof. Therefore, further improvement in the field of hindered amine light stabilizers is still desirable. The novel compounds of this invention address these shortcomings.

Hydrazides have been used to prevent deterioration of polyolefins by heat, oxidation or heavy metal contamination. Derivatives of hydrazides are also commercially available for use as polymer stabilizers. (See *Encyclopedia of Polymer Science and Engineering*, 2nd Ed. Vol. 2, pp 83–84 1985).

Definitions

As used herein, the term "acyl" refers to a substituent derived from a carboxylic acid group by removing the OH of the carboxyl group thereby providing a free valence, i.e. the acyl group derived from a generalized carboxylic acid D—C(=O)—OH would have the formula D—C(=O)— and would be referred to herein as a "D acyl" group.

As used herein, the terms "polymer" and "polymeric composition(s)" include homopolymers or any type of copolymers.

When any generalized functional group or index such as $R^1$, $R^2$, a, b, etc., appears more than once in a general formula, their meanings are independent of one another.

SUMMARY OF THE INVENTION

This invention is directed to compounds of formula I

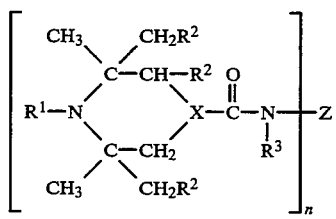

where $R^1$ is hydrogen, oxyl, hydroxyl, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–20 carbons, substituted or unsubstituted alicyclic acyl of 7–16 carbons, substituted or unsubstituted aromatic acyl of 7–11 carbons, substituted or unsubstituted araliphatic acyl of 7–22 carbons, —(C(=O))$_a$—N(R$^4$)(R$^5$), —(C(=O))$_a$—O—R$^6$, —(CH$_2$)$_a$—C(=O)—O—R$^7$ where a is 1–2, or —(CH$_2$—CH(R$^8$)—O)$_b$—R$^9$ where b is 2–50. Preferably $R^1$ is hydrogen, substituted or unsubstituted aliphatic of 1–4 carbons, substituted or unsubstituted araliphatic of 7–10 carbons, substituted or unsubstituted aliphatic acyl of 2–6 carbons or substituted or unsubstituted benzoyl. Most preferably $R^1$ is hydrogen, methyl, acetyl or benzoyl.

$R^2$ is hydrogen or aliphatic of 1–4 carbons. Preferably $R^2$ is hydrogen or methyl. Most preferably $R^2$ is hydrogen.

$R^3$ is hydrogen, substituted or unsubstituted aliphatic of 1–20 carbons, substituted or unsubstituted araliphatic of 7–22 carbons or substituted or unsubstituted alicyclic of 5–12 carbons. Preferably $R^3$ is hydrogen.

$R^4$ and $R^5$ are independently hydrogen, substituted or unsubstituted aliphatic of 1–20 carbons, substituted or unsubstituted aryl of 6–14 carbons, substituted or unsubstituted araliphatic of 7–22 carbons or substituted or unsubstituted alicyclic of 5–12 carbons which may optionally contain —N(R$^{10}$)— as a ring member and optionally $R^4$ and $R^5$ may be linked together through a heteroatom —N(R$^{10}$)— or —O— to form a heterocyclic ring of 5–7 atoms. Preferably $R^4$ and $R^5$ are independently hydrogen, substituted or unsubstituted aliphatic of 1–8 carbons, substituted or unsubstituted phenyl or substituted or unsubstituted benzyl. Most preferably $R^4$ is hydrogen, methyl or ethyl. Most preferably $R^5$ is substituted or unsubstituted aliphatic of 1–8 carbons, or substituted or unsubstituted phenyl.

$R^6$ is substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons. Preferably $R^6$ is substituted or unsubstituted aliphatic of 1–8 carbons, substituted or unsubstituted phenyl or substituted or unsubstituted benzyl.

$R^7$, $R^8$ and $R^9$ are independently hydrogen, substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons. Preferably $R^7$, $R^8$ and $R^9$ are independently hydrogen, substituted or unsubstituted aliphatic of 1–8 carbons, substituted or unsubstituted phenyl or substituted or unsubstituted benzyl.

$R^{10}$ is hydrogen, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–20 carbons, substituted or unsubstituted alicyclic acyl of 7–16 carbons, substituted or unsubstituted aromatic acyl of 7–11 carbons, substituted or unsubstituted araliphatic acyl of 7–22 carbons, —(C(=O))$_a$—N(R$^4$)(R$^5$), —(C(=O))$_a$—O—R$^6$, —(CH$_2$)$_a$—C(=O)—O—R$^7$ where a is 1–2, or —(CH$_2$—CH(R$^8$)—O)$_b$—R$^9$ where b is 2–50. Preferably $R^{10}$ is hydrogen, substituted or unsubstituted aliphatic of 1–4 carbons, substituted or unsubstituted araliphatic of 7–10 carbons, substituted or unsubstituted aliphatic acyl of 2–6 carbons or substituted or unsubstituted benzoyl. Most preferably $R^{10}$ is hydrogen, methyl, acetyl or benzoyl.

X is a triradical

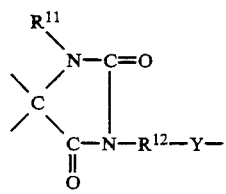

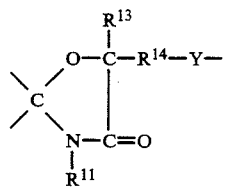

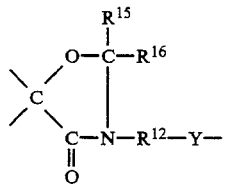

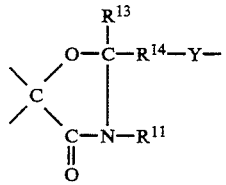

or

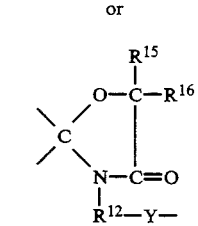

$R^{11}$ is independently of the same definition as $R^7$ and when alicyclic may optionally contain —N($R^{10}$)— as a ring member.

$R^{12}$ is substituted or unsubstituted aliphatic diradical of 1-20 carbons, substituted or unsubstituted aryl diradical of 6-12 carbons, substituted or unsubstituted alicyclic diradical of 5-12 carbons or substituted and unsubstituted araliphatic diradical of 7-22 carbons. The diradicals may optionally contain 1-6 heteroatoms —O—, —S—, and —N($R^{10}$)— with the proviso that multiple heteroatoms must be separated from each other by at least two carbon atoms and from the diradical ends by at least one carbon atom.

$R^{13}$ is independently of the same definition as $R^6$.

$R^{14}$ is independently of the same definition as $R^{12}$. When Y is a direct bond, $R^{14}$ may also be a direct bond.

$R^{13}$ and $R^{14}$ together with the carbon atom linking them may form a substituted or unsubstituted cycloalkyl ring of 5-12 carbons.

$R^{15}$ and $R^{16}$ are independently of the same definition as $R^{11}$ and may also be carbamoyl, alkoxycarbonyl of 2-5 carbons or pyridyl. $R^{15}$ and $R^{16}$ may be linked together to form an alicyclic of 5-12 carbons, or may be linked together through a heteroatom —O—, —S—, and —N($R^{10}$)— to form a heterocycle of 5-7 atoms. Preferably $R^{15}$ and $R^{16}$ are independently substituted or unsubstituted aliphatic of 1-20 carbons, substituted or unsubstituted alicyclic of 5-6 carbons, substituted or unsubstituted aryl of 6-10 carbons, substituted or unsubstituted araliphatic of 7-16 carbons, or may be linked together to form an alicyclic of 5-12 carbons or may be linked together to form a group of formula

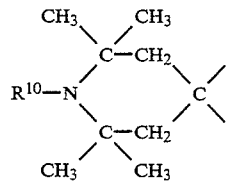

Y is —O—, —N($R^{11}$)— or a direct bond.

n is 1 or 2.

When n is 1, Z is

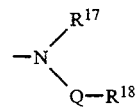

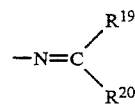

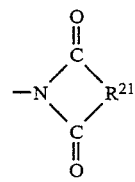

or

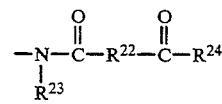

When n is 2, Z is

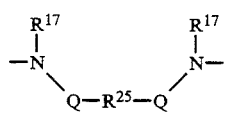

$R^{17}$ is independently of the same definition as $R^{11}$. Preferably $R^{17}$ is hydrogen, substituted or unsubstituted aliphatic of 1-12 carbons, substituted or unsubstituted alicyclic of 5-8 carbons, substituted or unsubstituted phenyl or substituted or unsubstituted araliphatic of 7-9 carbons. Most preferably $R^{17}$ is hydrogen, substituted or unsubstituted aliphatic of 1-10 carbons, substituted or unsubstituted cyclohexyl, substituted or unsubstituted phenyl or substituted or unsubstituted araliphatic of 7-14 carbons.

$R^{18}$ is independently of the same definition as $R^{11}$. Preferably $R^{18}$ is selected from hydrogen, substituted or unsubstituted aliphatic of 1-12 carbons, substituted or unsubstituted alicyclic of 5-8 carbons, substituted or unsubstituted phenyl or substituted or unsubstituted araliphatic of 7-9 carbons and when alicyclic $R^{18}$ may optionally contain 1-2 heteroatoms selected from —O— and —N($R^{10}$)— with the proviso stated above.

Most preferably $R^{18}$ is selected from hydrogen, substituted or unsubstituted aliphatic of 1–10 carbons, substituted or unsubstituted cyclohexyl, substituted or unsubstituted phenyl or substituted or unsubstituted araliphatic of 7–14 carbons and when alicyclic $R^{18}$ may be substituted piperidin-4-yl.

Q is $-C(=O)-$, $-S(=O)_2-$, $-C(=O)-O-$, $-[C(=O)]_2-O-$, $-C(=O)-N(R^{10})-$, $-[C(=O)]_2-N(R^{10})-$, $-C(=S)-N(R^{10})-$, $-C(=O)-R^{2\text{-}}$ $^2-C(=O)-N(R^{10})-$ or, when n is 1, a direct bond between the nitrogen and $R^{18}$. Preferably Q is $-C(=O)-$, $-C(=O)-O-$, $-[C(=O)]_2-O-$, $-C(=O)-N(R^{10})-$, $-C(=O)_2-N(R^{10})-$ or, when n is 1, a direct bond between the nitrogen and $R^{18}$.

$R^{19}$ and $R^{20}$ are independently of the same definition as $R^{11}$. $R^{19}$ and $R^{20}$ may be linked together to form a substituted or unsubstituted alicyclic ring of 5–12 carbons or may can be linked together through a heteroatom $-N(R^{10})-$, $-O-$ and $-S-$ to form a heterocyclic ring of 5–12 atoms. Preferably $R^{19}$ and $R^{20}$ are independently substituted or unsubstituted aliphatic of 1–8 carbons, substituted or unsubstituted alicyclic of 5–8 carbons, substituted or unsubstituted aryl of 6–12 carbons or substituted or unsubstituted araliphatic of 7–14 carbons, and $R^{19}$ and $R^{20}$ may be linked together to form a substituted or unsubstituted cycloalkyl ring of 5–8 carbons or a group of formula

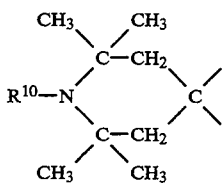

$R^{21}$ is substituted or unsubstituted aliphatic diradical of 2–200 carbons, substituted or unsubstituted aryl diradical of 6–14 carbons, substituted or unsubstituted alicyclic diradical of 5–12 carbons or substituted or unsubstituted araliphatic diradical of 7–22 carbons. The diradical chain(s) may optionally contain 1–6 heteroatoms $-O-$, $-S-$ and $-N(R^{10})-$ with the provisos that (a) multiple heteroatoms must be separated from each other by at least two carbon atoms and from the chain ends by at least one carbon atom, and that (b) the cyclic group formed contains 5–6 atoms in the ring. Preferably $R^{21}$ is substituted or unsubstituted aliphatic diradical of 2–18 carbons, substituted or unsubstituted ortho-phenylene or substituted or unsubstituted alicyclic diradical of 6–8 carbons. The diradical chain(s) may optionally contain 1–2 heteroatoms $-O-$ and $-N(R^{10})-$ with the provisos stated above.

$R^{22}$ is a direct bond or substituted or unsubstituted aliphatic diradical of 1–200 carbons, substituted or unsubstituted aryl diradical of 6–14 carbons, substituted or unsubstituted alicyclic diradical of 5–12 carbons or substituted or unsubstituted araliphatic diradical of 7–22 carbons. The diradical chain(s) may optionally contain 1–6 heteroatoms $-O-$, $-S-$, and $-N(R^{10})-$ with the proviso that multiple heteroatoms must be separated from each other by at least two carbon atoms and from the chain ends by at least one carbon atom. Preferably $R^{22}$ is substituted or unsubstituted aliphatic diradical of 2–18 carbons, substituted or unsubstituted phenylene or substituted or unsubstituted alicyclic diradical of 6–8 carbons. The diradical chain(s) may optionally contain 1–2 heteroatoms $-O-$ and $-N(R^{10})-$ with the proviso stated above.

$R^{23}$ is independently of the same definition as $R^{11}$. Preferably $R^{23}$ is hydrogen, substituted or unsubstituted aliphatic of 1–8 carbons, substituted or unsubstituted araliphatic of 7–8 carbons or substituted or unsubstituted alicyclic of 5–8 carbons.

$R^{24}$ is chosen from $-NH(R^{18})$, $-OH$ and $O^-M^+$, where M is sodium ion, potassium ion or ammonium ion. Preferably $R^{24}$ is $-OH$ or $-O^-M^+$ where M is sodium ion. Most preferably $R^{24}$ is $-OH$.

$R^{25}$ is substituted or unsubstituted aliphatic diradical of 1–20 carbons, substituted or unsubstituted aryl diradical of 6–12 carbons, substituted or unsubstituted alicyclic diradical of 5–12 carbons or substituted or unsubstituted araliphatic diradical of 7–22 carbons. The diradical chain(s) may optionally contain 1–6 heteroatoms selected from $-O-$ and $-N(R^{10})-$ with the proviso that multiple heteroatoms must be separated from each other by at least two carbon atoms and from the chain ends by at least one carbon atom. Preferably $R^{25}$ is substituted or unsubstituted aliphatic diradical of 2–12 carbons, substituted or unsubstituted aryl diradical of 6–12 carbons, substituted or unsubstituted alicyclic diradical of 5–12 carbons or substituted or unsubstituted araliphatic diradical of 7–12 carbons. The diradical chain(s) may optionally contain 1–2 heteroatoms selected from $-O-$ and $-N(R^{10})-$ with the proviso stated above. Most preferably $R^{25}$ is substituted or unsubstituted aliphatic diradical of 2–10 carbons, substituted or unsubstituted phenylene, substituted or unsubstituted alicyclic diradical of 5–8 carbons or substituted or unsubstituted araliphatic diradical of 7–12 carbons.

Optional substituents for $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{25}$ are one or more of the following: chloro, bromo, alkyl of 1–8 carbons, alkoxy of 1–12 carbons, phenoxy, cyano, hydroxy, epoxy, carboxy, benzoyl, benzoyloxy, dialkylamino of 2–8 carbons total, alkyoxycarbonyl of 2–6 carbons, acyloxy of 1–4 carbons, acryloyl, acryloyloxy, methacryloyl, methacryloyloxy, hydroxymethyl, hydroxyethyl, alkylthio of 1–4 carbons and trialkoxysilyl of 3–12 carbons. Additional optional substituents for $R^{21}$ and $R^{22}$ are alkyl of 5–180 carbons, alkylthio of 5–180 carbons, aralkylthio of 7–20 carbons, arylthio of 6–20 carbons, alkenyl of 2–180 carbons, cycloalkenyl of 5–12 carbons, aryl of 6–16 carbons, aralkyl of 7–17 carbons, aryloxy of 6–16 carbons, alkoxycarbonyl of 7–10 carbons, and (alkoxycarbonyl)alkylthio of 3–30 carbons. Additional substituents for $R^{18}$ are chosen from aliphatic of 1–20 carbons, cycloaliphatic of 5–12 carbons, aryl of 6–14 carbons, aralkyl of 7–22 carbons, alkoxy of 1–20 carbons, cycloalkoxy of 5–12 carbons, aryloxy of 6–14 carbons, aralkoxy of 7–15 carbons, aliphatic acyloxy of 2–20 carbons, alicyclic acyloxy of 6–13 carbons, aromatic acyloxy of 7–15 carbons, and araliphatic acyloxy of 8–16 carbons.

DESCRIPTION OF THE PREFERRED EMBODIMENTS

A. Generic Group Examples

As a substituted or unsubstituted aliphatic of 1–20 carbons, $R^1$, $R^3$, $R^4$, $R^5$, $R^6$, $R^7$, $R^8$, $R^9$, $R^{10}$, $R^{11}$, $R^{13}$, $R^{15}$, $R^{16}$, $R^{17}$, $R^{18}$, $R^{19}$, $R^{20}$ and $R^{23}$ are, for example, methyl, ethyl, n-propyl, isopropyl, butyl, allyl, hexyl, heptyl, octyl, nonyl, decyl, propargyl, octadecyl, dodecyl, isododecyl, tetradecyl, 2-methallyl, 2-hexenyl, 10-undecenyl, 2-dodecenyl, n-butyl, 2-hydroxyethyl, 2-butenyl, 2-hydroxyhexadecyl, 2-hydroxypropyl, 2-hexenyl, 10-undecenyl, 2-dodecenyl, 2-hydroxydodecyl, 2-hydroxy-5-hexenyl, 2-hydroxyhexyl, 2-hydroxydecyl, 2-hydroxyoctadecyl, 2-hydroxy-3-(methacryloyloxy)propyl, 2-hydroxy-3-(acryloyloxy)propyl, 2-hydroxy-3-phenoxypropyl, 2-hydroxy-3-(4-methoxyphenoxy)propyl, 2-hydroxy-3-isopropoxypropyl, 2-hydroxy-3-methoxypropyl, 2-hydroxy-3-(2-ethylhexyloxy)propyl, 2-hydroxy-3-(cyclohexyloxy)propyl, 2-hydroxy-3-(benzyloxy)propyl, 2-hydroxy-3-(benzoyloxy)propyl, 2-hydroxy-3-dodecyloxypropyl, 2-hydroxybutyl, 1-methyl-2-hydroxypropyl, cyanomethyl, 2,3-epoxypropyl or 2-(dimethylamino)ethyl.

As a substituted or unsubstituted alicyclic of 5–12 carbons, $R^1$, $R^3$, $R^4$, $R^5$, $R^6$, $R^7$, $R^8$, $R^9$, $R^{10}$, $R^{11}$, $R^{13}$, $R^{15}$, $R^{16}$, $R^{17}$, $R^{18}$, $R^{19}$, $R^{20}$ and $R^{23}$ are, for example, cyclohexyl, trimethylcyclohexyl, cyclooctyl, cyclododecyl, 4-t-butylcyclohexyl, 2-hydroxycyclododecyl, 3-cyclohexenyl, 2-hydroxycyclohexyl, 2-hydroycyclopentyl, cyclododecyl, 4-octylcyclohexyl or 2-methyl-4-octylcyclohexyl.

As substituted or unsubstituted aryl of 6–14 carbons $R^4$, $R^5$, $R^6$, $R^7$, $R^8$, $R^9$, $R^{11}$, $R^{13}$, $R^{15}$, $R^{16}$, $R^{17}$, $R^{18}$, $R^{19}$, $R^{20}$ and $R^{23}$ are, for example, phenyl, tolyl, 4-chlorophenyl, isopropylphenyl, isopropenylphenyl, anisyl, 3,5-di(t-butyl)-4-hydroxyphenyl, 3,5-di(t-amyl)-4-hydroxyphenyl, 3-(t-butyl)-5-methyl-4-hydroxyphenyl, naphthyl, 3-methyl-5-t-butyl-4-hydroxyphenyl, 3,4,5-trimethoxyphenyl or 4-(dimethylamino)phenyl.

As a substituted of unsubstituted araliphatic group of 7–22 carbons, $R^1$, $R^3$, $R^4$, $R^5$, $R^6$, $R^7$, $R^8$, $R^9$, $R^{10}$, $R^{11}$, $R^{13}$, $R^{15}$, $R^{16}$, $R^{17}$, $R^{18}$, $R^{19}$, $R^{20}$ and $R^{23}$ are, for example, benzyl, 3-methylbenzyl, 4-t-butylbenzyl, cinnamyl, 3,5-di-t-butyl-4-hydroxybenzyl, 2-hydroxy-2-phenylethyl, 2-phenylethyl, cumyl, trimethylbenzyl, 4-octyloxybenzyl, naphthylmethyl, or (4-dodecylphenyl)methyl, 2-(3,5-di-t-butyl-4-hydroxyphenyl)ethyl, 2-(3,5-di-t-amyl-4-hydroxyphenyl)ethyl or 2-(3-t-butyl-5-methyl-4-hydroxyphenyl)ethyl.

As a substituted or unsubstituted aliphatic acyl of 2–20 carbons, substituted or unsubstituted alicyclic acyl of 7–16 carbons, substituted or unsubstituted aromatic acyl of 7–11 carbons, or substituted or unsubstituted araliphatic acyl of 7–22 carbons, $R^1$ and $R^{10}$ are, for example, formyl, acetyl, chloroacetyl, acryloyl, methacryloyl, propionyl, butyryl, 2-methylpropionyl, caproyl, capryloyl, lauroyl, crotonoyl, stearoyl, octadecanoyl, cyclohexylcarbonyl, 4-t-butylcyclohexylcarbonyl, 3-cyclohexenyl-1-carbonyl, cyclododecylcarbonyl, 4-octylcyclohexylcarbonyl, 2-ethoxy-2-oxoacetyl, 2-methoxy-2-oxoacetyl, 2-methyl-4-octylcyclohexylcarbonyl, benzoyl, toluoyl, 4-chlorobenzoyl, isopropylbenzoyl, anisoyl, hydroxybenzoyl, 3,5-di-t-butyl-4-hydroxybenzoyl, naphthoyl, 3-methyl-5-t-butyl-4-hydroxybenzoyl, 3,4,5-trimethoxybenzoyl, 4-dimethylaminobenzoyl, 3-(3,5-di-t-butyl-4-hydroxyphenyl)-propionyl, cinnamoyl or dihydrocinnamoyl; preferably alkanoyl of 2–5 carbons, cyclohexylcarbonyl, benzoyl or phenacyl.

As —(C(=O))$_a$—N($R^5$)($R^4$) wherein optionally $R^4$ and $R^5$ may be linked together through a heteroatom —N($R^{10}$)— or —O— to form a heterocylic ring of 5–7 atoms, $R^1$ and $R^{10}$ are, for example, N-methylcarbamoyl, N-butylcarbamoyl, N-octadecylcarbamoyl, N-dodecylcarbamoyl, N,N-dimethylcarbamoyl, N,N-diethylcarbamoyl, N-cyclohexylcarbamoyl, N,N-dihexylcarbamoyl, piperidin-1-ylcarbonyl, 2,2,6,6-tetramethyl-4-piperidinylcarbonyl, piperazine-1-carbonyl, 4-methylpiperazine-1-carbonyl, morpholin-1-carbonyl, 2-(dibutylamino)-2-oxoacetyl, 2-(phenylamino)-2-oxoacetyl, N-phenylcarbamoyl, N-benzylcarbamoyl, N-(4-butylphenyl)carbamoyl, N-(alpha-naphthyl)carbamoyl, N-phenyl-N-hexylcarbamoyl, N-(trimethylphenyl)-N-amylcarbamoyl, N,N-diphenylcarbamoyl, N,N-di-(4-methylphenyl)carbamoyl or N-(4-benzylaminophenyl)-N-phenylcarbamoyl.

As —(C(=O))$_a$—O—$R^6$, $R^1$ and $R^{10}$ are, for example, methoxycarbonyl, 2-ethoxy-2-oxoacetyl, 2-methoxy-2-oxoacetyl, 2-cyclohexyloxy-2-oxoacetyl, 2-octadecyloxy-2-oxoacetyl, ethoxycarbonyl, phenoxycarbonyl, methallyloxycarbonyl, (2-methylphenoxy)carbonyl, allyloxycarbonyl, cyclopentoxycarbonyl, cyclohexoxycarbonyl, cyclododecyloxycarbonyl, (2-ethylhexyl)oxycarbonyl, ethoxycarbonyl, isopropoxycarbonyl or (4-octyloxyphenyl)carbonyl.

As —(CH$_2$)$_a$—C(=O)—O—$R^7$, $R^1$ and $R^{10}$ are, for example, methoxycarbonylmethyl, 2-(methoxycarbonyl)ethyl, butoxycarbonylmethyl, (benzyloxy)carbonylmethyl or 2-(benzyloxycarbonyl)ethyl.

As —(CH$_2$—CH($R^8$)—O)$_b$—$R^9$, $R^1$ and $R^{10}$ are, for example, nonylphenoxypoly(ethoxy)ethyl, butoxypoly(propoxy)ethyl, benzyloxypoly(ethoxy)ethyl, hydroxypoly(ethoxy)ethyl or 2-[hydroxypoly(propoxy)]-2-methylethyl.

As an aliphatic group of 1 to 4 carbons, $R^2$ is, for example, methyl, ethyl, propyl, isopropyl, butyl, sec-butyl or t-butyl.

As a substituted or unsubstituted aliphatic diradical of 1–20 carbon, substituted or unsubstituted aryl diradical of 6–12 carbons, substituted or unsubstituted alicyclic diradical of 5–12 carbons and substituted or unsubstituted araliphatic diradical of 7–22 carbons, said diradicals containing 1–6 heteroatoms —O—, —S—, and —N($R^{10}$)—, $R^{12}$ and $R^{14}$ are, for example, 1,2-ethanediyl, methylene, 1,2-propenediyl, 1-phenyl-1,2-ethanediyl, 1,3-hexanediyl, 1,4-butanediyl, 1,2-cyclohexanediyl, 1,2-phenylene, 1,3-phenylene, 1,4-phenylene, 4-methyl-4-cyclohexene-1,2-diyl, 4-cyclohexene-1,2-diyl, 4-methylcyclohexane-1,2-diyl, propane-2,2-bis[4-cyclohexyl], 3-oxapentane-1,5-diyl, methylenebis[4-cyclohexyl], 1,2-phenylenebis(methyl), 1,3-phenylenebis(methyl), 1,4-phenylenebis(methyl), biphenyl-4,4'-diyl, biphenyl-3,3'-diyl, biphenyl-3,4'-diyl, methylenebis[phenylene], 1,2-propanediyl, 1,3-propanediyl, 1,4-butanediyl, 1,18-octadecanediyl, 2,2-dimethyl-1,3-propanediyl, 2-methylpentane-2,4-diyl, 1,10-decanediyl, 1,12-dodecanediyl, 3-oxapentane-1,5-diyl, 4-oxaheptane-1,7-diyl, 3,6-dioxaoctane-1,8-diyl, 4,9-dioxadodecane-1,12-diyl, 4-methyl-4-azaheptane-1,4-diyl, 3,6-diaza-3,6-dimethyl-1,8-octanediyl, 3-methyl-3-azapentane-1,5-diyl, 1,2-cyclohexanediyl or 1,4-cyclohexanediyl.

When linked together with the carbon atom linking them forming a cycloalkyl ring of 5–12 carbons, $R^{13}$ and $R^{14}$ form, for example, cyclopentyl, cyclohexyl, cycloheptyl, t-butylcyclohexyl, methylcyclohexyl, cyclooctyl, and cyclododecyl.

When alkoxycarbonyl of 2–5 carbons, $R^{15}$ and $R^{16}$ are, for example, methoxycarbonyl, ethoxycarbonyl, isopropoxycarbonyl and butoxycarbonyl.

When taken together with the carbon to which they are attached can form a substituted or unsubstituted saturated alicyclic group of 5–12 carbons or linked together through a heteroatom —O—, —S— and —N(R¹⁰)— to form a heterocycle of 5–7 atoms, R¹⁵ and R¹⁶ are, for example, cyclopentyl, cyclohexyl, cycloheptyl, cyclooctyl, cyclododecyl, 4-oxacyclohexyl, 3,5-dimethylcyclohexyl, 4-thiacyclohexyl, 2,2,6,6-tetramethyl-4-piperidinyl, 3,3,5-trimethylcyclohexyl, 3-methoxycyclohexyl, 4-t-butylcyclohexyl, cycloundecyl and 3,3,5,5-tetramethylcyclohexyl.

When alicyclic and optionally containing —N(R¹⁰)— as a ring member, R⁴, R⁵, R¹¹, R¹⁵, R¹⁶, R¹⁷, R¹⁸, R¹⁹, R²⁰, and R²³ are, for example, 2,2,6,6-tetramethyl-4-piperidinyl, 2,6-diethyl-1,2,3,6-tetramethyl-4-piperidinyl, 1-acetyl-2,2,6,6-tetramethyl-4-piperidinyl and 1-(4-methylbenzoyl)-2,6-dimethyl-2,6-dipropyl-3-ethyl-4-piperidinyl.

When linked together to form a substituted or unsubstituted alicyclic of 5–12 carbons, or when linked together by —N(R¹⁰)—, —O— or —S—, R¹⁹ and R²⁰ form, for example, cyclopentyl, cyclohexyl, cycloheptyl, 4-t-butylcyclohexyl, 2-methylcyclohexyl, cyclooctyl, 2,2,6,6-tetramethyl-4-piperidinyl, 2,6-diethyl-2,3,6-trimethyl-4-piperidinyl, 1,2,2,6,6-pentamethyl-4-piperidinyl, 1-acetyl-2,2,6,6-tetramethyl-4-piperidinyl, 1-ethyl-2,2,6,6-tetramethyl-4-piperidinyl, 4-oxacyclohexyl, and 4-thiacyclohexyl.

As a substituted or unsubstituted aliphatic diradical of 2–200 carbons, substituted or unsubstituted aryl diradical of 6–14 carbons, substituted or unsubstituted alicyclic diradical of 5–12 carbons, or substituted or unsubstituted araliphatic diradical of 7–22 carbons, any of which may optionally contain 1–6 heteroatoms selected from —O—, —S—, and —N(R¹⁰)— with the provisos that (a) multiple heteroatoms must be separated from each other by at least two carbon atoms and from the chain ends by at least one carbon atom and that (b) the cyclic group formed contains 5–6 atoms in the ring, R²¹ is, for example, 1,2-ethanediyl, 1,2-ethenediyl, 1,3-propanediyl, 1,2-propenediyl, 2-thiapropane-1,3-diyl, 2-oxapropane-1,3-diyl, 1-chloro-1,2-ethenediyl, 1-phenyl-1,2-ethenediyl, 1,3-hexanediyl, 2-azapropane-1,3-diyl, 2-methyl-2-azapropane-1,3-diyl, 1,2-cyclohexanediyl, 1,2-phenylene, 4-methyl-4-cyclohexene-1,2-diyl, 4-cyclohexene-1,2-diyl, 4-methylcyclohexane-1,2-diyl, norbornane-2,3-diyl, 5-norbornene-2,3-diyl, bicyclo[2.2.2]octane-2,3-diyl, bicyclo[2.2.2]oct-5-ene-2,3-diyl, bicyclo[2.2.1]heptane-1,2-diyl, bicyclo[2.2.1]heptane-1,2-diyl, 4-carboxy-1,2-phenylene, 4-methoxycarbonyl-1,2-phenylene, 1-(substituted)ethane-1,2-diyl wherein the substituent is chosen from hydrogen, chloro, phenyl, methyl, ethyl, propyl, butyl, hexyl, octyl, decyl, dodecyl, hexadecyl, octadecyl, hexenyl, isohexenyl, diisobutenyl, decenyl, dodecenyl, isododecenyl, octenyl, nonenyl, tetradecenyl, hexadecenyl, octadecenyl, isooctadecenyl, triacontenyl, and polyisobutenyl; 1-(substituted)ethane-1,2-diyl, 5-(substituted)norbornane-2,3-diyl, 5-(substituted)bicyclo[2.2.2]octane-2,3-diyl, and 4-(substituted)cyclohexane-1,2-diyl wherein the substituent is chosen from methylthio, ethylthio, butylthio, hexylthio, octylthio, hexadecylthio, octadecylthio, 2-hydroxyethylthio, phenylthio, benzylthio, (3,5-di-t-butyl-4-hydroxy)phenylthio, and (3-t-butyl-5-methyl-4-hydroxyphenyl)benzylthio.

As a substituted or unsubstituted aliphatic diradical of 1–200 carbons, substituted or unsubstituted aryl diradical of 6–14 carbons, substituted or unsubstituted alicyclic diradical of 5–12 carbons, or substituted or unsubstituted araliphatic diradical of 7–22 carbons, any of which may optionally contain 1–6 heteroatoms selected from —O—, —S—, and —N(R¹⁰)— with the proviso that multiple heteroatoms must be separated from each other by at least two carbon atoms and from the chain ends by at least one carbon atom, R²² is, for example, methylene, 1,2-ethanediyl, 1,2-ethenediyl, 1,3-propanediyl, 1,2-propenediyl, 2-thiapropane-1,3-diyl, 3-thiapentane-1,2-diyl, 2-oxapropane-1,3-diyl, 1-chloro-1,2-ethenediyl, 1-phenyl-1,2-ethenediyl, 1,3-hexanediyl, 2-azapropane-1,3-diyl, 2-methyl-2-azapropane-1,3-diyl, 1,2-cyclohexanediyl, 1,2-phenylene, 4-methyl-4-cyclohexene-1,2-diyl, 4-cyclohexene-1,2-diyl, 4-methylcyclohexane-1,2-diyl, norbornane-2,3-diyl, 5-norbornene-2,3-diyl, bicyclo[2.2.2]octane-2,3-diyl, bicyclo[2.2.2]oct-5-ene-2,3-diyl, bicyclo[2.2.1]heptane-1,2-diyl, bicyclo[2.2.1]heptane-1,2-diyl, 4-carboxy-1,2-phenylene, 4-methoxycarbonyl-1,2-phenylene, propane-2,2-bis[4-cyclohexyl], 3-oxapentane-1,5-diyl, methylenebis[4-cyclohexyl], 1,2-, 1,3-, or 1,4-phenylene, 1,2-, 1,3-, or 1,4-phenylenebis(methyl), or 2,5-diazahexane-1,6-diyl; biphenyl-4,4'-diyl, biphenyl-3,3'-diyl, biphenyl-3,4'-diyl, methylenebis[phenylene], 1-(substituted)ethane-1,2-diyl wherein the substituent is chosen from hydrogen, chloro, phenyl, methyl, ethyl, propyl, butyl, hexyl, octyl, decyl, dodecyl, hexadecyl, octadecyl, hexenyl, isohexenyl, diisobutenyl, decenyl, dodecenyl, isododecenyl, octenyl, nonenyl, tetradecenyl, hexadecenyl, octadecenyl, isooctadecenyl, triacontenyl, and polyisobutenyl; 1-(substituted)ethane-1,2-diyl, 5-(substituted)norbornane-2,3-diyl, 5-(substituted)bicyclo[2.2.2]octane-2,3-diyl, and 4-(substituted)cyclohexane-1,2-diyl wherein the substituent is chosen from methylthio, ethylthio, butylthio, hexylthio, octylthio, hexadecylthio, octadecylthio, 2-hydroxyethylthio, phenylthio, benzylthio, (3,5-di-t-butyl-4-hydroxy)phenylthio, and (3-t-butyl-5-methyl-4-hydroxyphenyl)benzylthio.

As a substituted or unsubstituted aliphatic diradical of 1–20 carbons, substituted or unsubstituted aryl diradical of 6–12 carbons, substituted or unsubstituted alicyclic diradical of 5–12 carbons, or substituted or unsubstituted araliphatic diradical of 7–22 carbons, the diradical chain(s) optionally contain 1–6 heteroatoms selected from —O—, —S—, and —N(R¹⁰)— with the proviso that multiple heteroatoms must be separated from each other by at least two carbon atoms and from the chain ends by at least one carbon atom, R²⁵ is, for example, methylene, ethane-1,2-diyl, ethene-1,2-diyl, propane-1,3-diyl, propene-1,2-diyl, 2-thiapropane-1,3-diyl, 2-oxapropane-1,3-diyl, hexane-1,3-diyl, 2-azapropane-1,3-diyl, 2-methyl-2-aza-propane-1,3-diyl, cyclohexane-1,2-diyl, 1,2-phenylene, 1,3-phenylene, 1,4-phenylene, hexane-1,6-diyl, octane-1,8-diyl, decane-1,10-diyl, dodecane-1,12-diyl, 3-hexene-1,6-diyl, 4-methyl-1,2-phenylene, 4-chloro-1,2-phenylene, 4-methylcyclohexane-1,2-diyl, cyclohexane-1,2-diyl, 4-methyl-4-cyclohexene-1,2-diyl, toluene-alpha,2-diyl, toluene-alpha,3-diyl, toluene-alpha,4-diyl, 3,3'-dimethoxybiphenyl-4,4'-diyl, 3,3'-dimethylbiphenyl-4,4'-diyl, methylenebis(4-phenyl), methylenebis(4-cyclohexyl) and isophoronediyl.

B. Examples of Compounds

Examples of the hindered amine light stabilizers of this invention include the following non-limiting list:

1. 3-acetyl-2,2,4,4-tetramethyl-20-[4,5,7-triaza-3-oxo-6-(thiooxo)undecyl]-7-oxa-3,20-diazadispiro[5.1.11.2]-heneicosan-21-one 2. 2,4-diethyl-1,2,3,4-tetramethyl-14-{2-[N-(n-hexadecylsuccinimidyl)amino] -2-oxoethyl}-7-oxa-3,14-diazadispiro[5.1.5.2]pentadecan-15-one
3. 14,14'-{4,5,7,14,16,17-hexaaza-3,6,15,18-tetraoxaeicosane-1,20-diyl}bis{2,2,4,4,-tetramethyl-7-oxa-3,14-diazadispiro[5.1.4.2]tetradecane-13-one}
4. 8-allyl-7,7,9,9-tetramethyl-1,3,8-triaza-3-[4-hydrazino-4-oxobutyl]spiro[4.5]decane-2,4-dione
5. 2,2,4,4-tetramethyl-14-{4,5,7-triaza-3,6-dioxopentacosanyl}-7-oxa-3,14-diazatrispiro[5.1.11.2]heneicosane-21-one
6. 8-(2-acetoxyethyl)-2,7,7,9,9-pentamethyl-2-(4,5-diaza-3,6-dioxoheptyl)-3,8-diaza-1-oxaspiro[4.5]decane-4-one
7. 2,8-dibutyl-4,7,7,9,9-pentamethyl-2-[2-hydrazino-2-oxoethyl]-1-oxa-4,8-diazaspiro[4.5]decane-3-one, hydrazone of 2,2,6,6-tetramethyl-4-piperidone
8. 2,2,4,4-tetramethyl-20-[6,6-dimethyl-4,5-diaza-3-oxoheptyl]-7-oxa-3,20-diazadispiro[5.1.11.2]heneicosane-21-one
9. 2,2,4,4-tetramethyl-20-{3-[N-(maleimido)amino]-3-oxopropyl}-7-oxa-3,20-diazadispiro[5.1.11.2]heneicosane-21-one
10. 2,2,4,4-tetramethyl-20-[3-hydrazino-3-oxopropyl]-7-oxa-3,20-diazadispiro[5.1.11.2]heneicosane-21-one, hydrazone of 2-pentanone
11. 1-benzyl-2,2,4,4-tetramethyl-20-[4,5-diaza-8-oxo-3,6-dioxa-9-carboxynonyl]-7-oxa-3,20-diazadispiro[5.1.11.2]heneicosane-21-one
12. 2,2-dipropyl-3-[4,5-diaza-3,6-dioxo-7-oxatridecyl]-6-phenyl-7,8-dimethyl-7,8-dibenzyl-1-oxa-3,8-diazaspiro[4.5]decane-4-one
13. 2,2,4,4-tetramethyl-20-[4,5,8-triaza-3,6,7-trioxo-8-di(2,2,6,6-teteamethyl-4-piperidinyl)octyl]7-oxa-3,20-diazadispiro[5.1.11.2]heneicosan-21-one
14. 9,9'-[diphenylmethane-4,4'-diylbis(1,3,4-triaza-2,5-dioxohex-6-yl]bis{7,7,9,9-tetramethyl-1,3,8-triazaspiro[4.5]decane-2,4-dione}
15. 1,7,7,8,9,9-hexamethyl-3-[5-methyl-8-carboxy-4,5-diaza-3,6-dioxooctyl]-1,3,8-triazaspiro[4.5]decane-2,4-dione, sodium salt
16. 2,2,4,4-tetramethyl-3-[(4-methoxyphenyl)methoxycarbonyl]-20-[8-(4-methoxyphenyl)-4,5-diaza-7-oxa-3,6-dioxooctyl]-7-oxa-3,20-diazadispiro[5.1.11.2-]heneicosane-21-one
17. 2,2,4,4-tetramethyl-20-{3-[(tetrahydro-4-methylphthalimido)amino]-3-oxopropyl}-7-oxa-3,20-diazadispiro[5.1.11.2]heneicosane-21-one
18. 2,2,4,4-tetramethyl-3-(2-hydroxyoctadecyl)-20-[7-(2-hydroxyoctadecyl)-7-hydroxy-4,5-diaza-3-oxotricosanyl]-7-oxa-3,20-diazadispiro[5.1.11.2]heneicosane- 21-one
19. 2,7,7,9,9-pentamethyl-2-phenyl-8-(2-hydroxypropyl)-4-[6-hydroxy-2-oxo-4-(2-hydroxypropyl)-3,4-diazaheptyl]-1-oxa-4,8-diazaspiro[4.5]decane-3-one
20. 2,2,3,4,4-pentamethyl-3-[7-(4-(ethoxycarbonyl)phthalimido-3-thia-7-aza-6-oxoheptyl]-7-oxa-3,20-diazadispiro[5.1.11.2]heneicosane-21-one

C. Utility

The novel stabilizers of this invention are very effective additives for the stabilization of polymeric compositions which are normally subject to thermal, oxidative or actinic light degradation. At times it may be beneficial to add extraneous additives which will act as synergists with the hindered amine light stabilizing groups.

The novel stabilizers of this invention can be blended with various polymeric compositions in high concentrations to form masterbatches which can then be blended with additional polymer either of the same or different type.

The stabilizing effective amount of stabilizer used to stabilize the polymeric composition will depend on the particular polymer system to be stabilized, the degree of stabilization desired and the presence of other stabilizers in the composition. Normally it is advisable to have about 0.01 to about 5% by weight of the 2,2,6,6-tetraalkylpiperidine moiety present in the polymeric composition. An advantageous range is from about 0.05 to about 2% by weight of the 2,2,6,6-tetraalkylpiperidine portion of the molecule in the final composition. In most cases 0.1 to about 1% by weight is sufficient.

The hindered amine light stabilizers of this invention are also intermediates for the polymer bound hindered amine light stabilizers disclosed and claimed in U.S. Pat. No. 4,857,595.

Examples of polymeric compositions which may be stabilized by these novel hindered amine light stabilizers include:

1. Polyolefins such as high, low and linear low density polyethylenes, which may be optionally cross-linked, polypropylene, polyisobutylene, poly(methylbutene-1), polyacetylene and in general polyolefins derived from monomers having from two to about ten carbon atoms and mixtures thereof.
2. Polyolefins derived from diolefins such as polybutadiene and polyisoprene.
3. Copolymers of mono or diolefins such as ethylene-propylene, propylene-butene-1, propylene-isobutylene and ethylene-butene-1 copolymer.
4. Terpolymers of ethylene and propylene with dienes (EPDM) such as butadiene, hexadiene, dicyclopentadiene and ethylidene norbornene.
5. Copolymers of alpha-olefins with acrylic acid or methacrylic acids or their derivatives such as ethylene-acrylic acid, ethylene-methacrylic acid and ethylene-ethyl acrylate copolymers.
6. Styrenic polymers such as polystyrene (PS) and poly(p-methylstyrene).
7. Styrenic copolymers and terpolymers such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers such as butadiene (ABS), polyisoprene or styrene-butadiene-styrene block copolymers, graft copolymers of styrene-methyl methacrylate on rubbers such as polybutadiene (MBS), butadiene-styrene radial block copolymers (e.g. KRO 3 of Phillips Petroleum Co.), selectively hydrogenated butadiene-styrene block copolymers (e.g. Kraton G from Shell Chemical Co.) and mixtures thereof.
8. Polymers and copolymers derived from halogen-containing vinyl monomers such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride-vinyl acetate copolymers and ethylene-tetrafluoroethylene copolymers.
9. Halogenated rubbers such as chlorinated and/or brominated butyl rubbers or polyolefins and fluoroelastomers.
10. Polymers and copolymers derived from alpha, beta-unsaturated acids, anhydrides, esters, amides and nitriles or combinations thereof such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the above polymers and various blends and mixtures thereof as well as rubber modified versions of the above polymers and copolymers.
11. Polymers and copolymers derived from unsaturated alcohols or their acylated derivatives such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.
12. Polymers and copolymers derived from unsaturated amines such as poly(allyl melamine).
13. Polymers and copolymers derived from epoxides such as polyethylene oxide, polypropylene oxide and copolymers thereof as well as polymers derived from bis-glycidyl ethers.
14. Poly(phenylene oxides), poly(phenylene ethers) and modifications thereof containing grafted polystyrene or rubbers as well as their various blends with polystyrene, rubber modified polystyrenes or nylon.
15. Polycarbonates and especially the aromatic polycarbonates such as those derived from phosgene and bisphenols such as bisphenol-A, tetrabromobisphenol-A and tetramethylbisphenol-A.
16. Polyester derived from dicarboxylic acids and diols and/or hydroxycarboxylic acids or their corresponding lactones such as polyalkylene phthalates (e.g. polyethylene terephthalate (PET), polybutylene terephthalate (PBT), and poly(1,4-dimethylcyclohexane terephthalate) or copolymers thereof) and polylactones such as polycaprolactone.
17. Polyarylates derived from bisphenols (e.g. bisphenol-A) and various aromatic acids such as isophthalic and terephthalic acids or mixtures thereof.
18. Aromatic copolyestercarbonates having carbonate as well as ester linkages present in the backbone of the polymers such as those derived from bisphenols, iso- and terephthaloyl chlorides and phosgene.
19. Polyurethanes and polyureas.
20. Polyacetals such as polyoxymethylenes and polyoxymethylenes which contain ethylene oxide as a comonomer.
21. Polysulfones, polyethersulfones and polyimidesulfones.
22. Polyamides and copolyamides which are derived from diamines and dicarboxylic acids and/or from aminocarboxylic acids or the corresponding lactams such as the following nylons: 6, 6/6, 6/10, 11 and 12.
23. Polyimides, polyetherimides, polyamideimides and copolyetheresters.
24. Cross-linked polymers which are derived from aldehydes on the one hand and from phenols, ureas and melamine on the other hand such as phenol-formaldehyde, urea-formaldehyde and melamine-formaldehyde resins.
25. Alkyd resins such as glycerol-phthalic acid resins and mixtures thereof with melamine-formaldehyde resins.
26. Blends of vinyl monomers and unsaturated polyester resins which are derived from copolyesters of saturated and unsaturated dicarboxylic acids with polyhydric alcohols as well as from vinyl compounds (crosslinking agents) and also halogen-containing, flame resistant modifications thereof.
27. Natural polymers such as cellulose, natural rubber as well as the chemically modified homologous derivatives thereof such as cellulose acetates, cellulose propionate, cellulose butyrate and the cellulose ethers such as methyl and ethyl cellulose.

In addition the novel stabilizers of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber-modified styrenics or nylon.

The novel hindered amine light stabilizers of this invention can be used together with other additives to further enhance the properties of the finished polymer. Examples of other additives that can be used in conjunction with the stabilizers of this invention include antioxidants such as alkylated monophenols, alkylated hydroquinones, hydroxylated thiodiphenyl ethers, alkylidene-bisphenols, hindered phenolic benzyl compounds, acylaminophenols, esters of 3-(3,5-di-t-butyl-4-hydroxyphenyl)- propionic acid, esters of 3-(5-t-butyl-4-hydroxy-3-methylphenyl)propionic acid, 3-(3,5-di-t-butyl-4-hydroxyphenyl)propionic acid amides; UV absorbers and light stabilizers such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers; other additives such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and nondripping agents, melt flow improvers and antistatic agents. Numerous examples of suitable additives of the above type are given in Canadian Patent 1,190,038.

Thus, the compounds of this invention are efficient light stabilizers for both natural and artificial polymeric compositions also providing the thermal stability usually associated with the hydrazide functionality. In addition, the hydrazide functionality permits further derivatives to be prepared. The ability to prepare further derivatives permits further modification of the stabilizer properties. These include greater comparability with the polymeric composition in which it is intended to be incorporated and frequently greater efficiency. The hydrazide group reacts readily with many functional groups contained in polymeric or monomeric compounds, such as anhydrides, esters, ketones, aldehydes, chloroformates, acid halides and isocyanates.

D. Preparative Methods

The novel HALS hydrazides are prepared by reacting (2,2,6,6- tetraalkylpiperidinyl)esters with a primary or secondary alkyl hydrazine, hydrazine or hydrazine hydrate. The reaction is illustrated by the following equations.

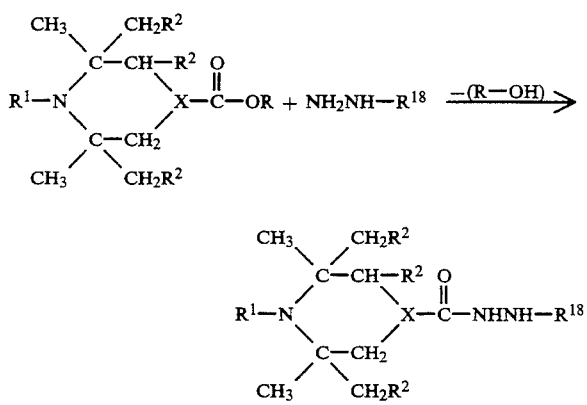

where $R^1$, $R^2$, $R^{18}$ and X are as previously defined and R is alkyl of 1 to 20 carbons or phenyl.

Typically the ester is dissolved in a polar solvent and converted to the desired hydrazide by stirring with an equivalent amount or slight excess of a primary or secondary alkylhydrazine, hydrazine or hydrazine hydrate. The reaction may go at room temperature or may require heating. Preferably the hydrazinolysis reaction is carried out in methanol or ethanol at 10°–30° C. but other solvents such as isopropanol or ethylene glycol are also acceptable. In most cases the resulting hydrazides can be purified by recrystallization from the lower alcohols.

The starting esters are known in the literature as described in U.S. Pat. Nos. 3,941,744, 3,975,462, 4,005,094, 4,241,208, 4,408,051, 4,526,966, 4,562,220, 4,689,416, 4,745,192, 4,755,602 and DE 3,523,679.

Examples of suitable hydrazines include hydrazine, hydrazine hydrate, 35–85% hydrazine hydrate, methylhydrazine, ethylhydrazine, propylhydrazine, isopropylhydrazine, n-butylhydrazine, sec-butylhydrazine, n-amylhydrazine, sec-amylhydrazine, n-hexylhydrazine and n-octylhydrazine and sec-octylhydrazine.

Hydrazone derivatives of this invention are prepared by reacting the hydrazides with ketones, aldehydes or formaldehyde in inert solvents, preferably in hydrocarbon solvents under azeotropic conditions.

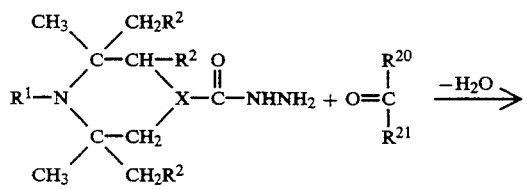

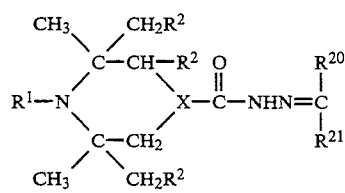

where $R^1$, $R^2$, $R^{20}$, $R^{21}$ and X are as previously defined.

They may also be prepared by reacting hydrazones of ketones or aldehydes with esters described in the literature (cited above).

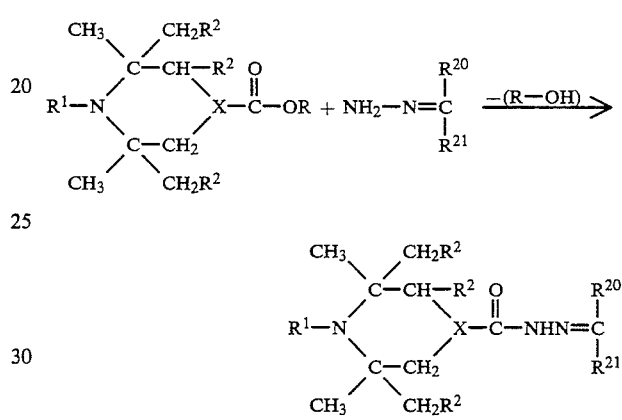

where $R^1$, $R^2$, $R^{20}$, $R^{21}$, R and X are as previously defined.

The novel carbamoyl and thiocarbamoyl derivatives are prepared by reacting the hydrazides with isocyanates, diisocyanates, isothiocyanates or diisothiocyanates in aprotic polar solvents such as tetrahydrofuran or dimethylformamide.

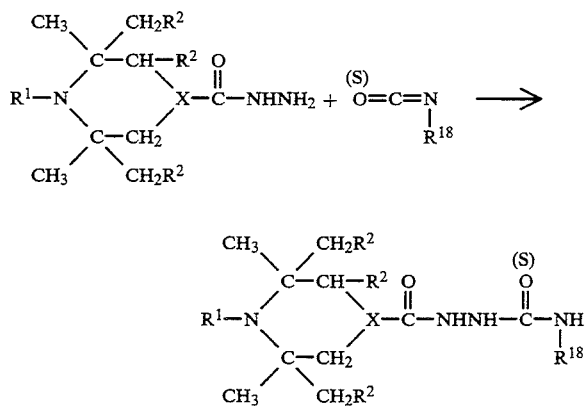

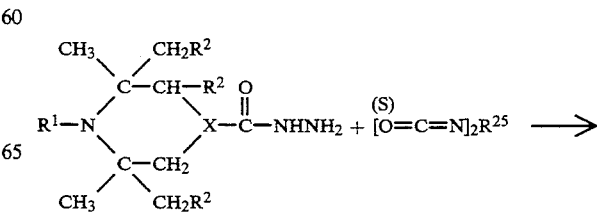

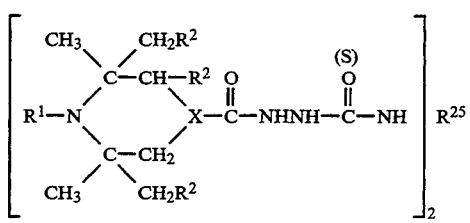

where $R^1$, $R^2$, $R^{18}$, $R^{25}$ and X are as previously defined.

The reactions of hydrazides with ketones, aldehydes, isocyanates, diisocyanates, isothiocyanates, and diisothiocyanates are well known in the art and can occur under a wide variety of temperatures, times, solvents and concentrations. Generally a mole ratio of 0.9 to 1.0 to 1.1 to 1.0 of the hydrazide to the monofunctinal coreactant is employed. If the coreactant is difunctional, then a mole ratio of 1.8 to 2.0 to 1.1 to 1.0 of the hydrazide to the difunctional coreactant is employed. If the coreactant is a compound that can easily be removed from the product, e.g. acetone or methyl ethyl ketone, lower mole ratios may be desireable. In fact it may be desireable to use the coreactant as the solvent.

The hydrazides also react with unsubstituted or N-substituted amic acid esters in lower alcohol solutions to form diacyl hydrazines.

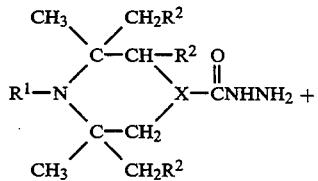

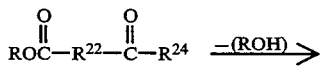

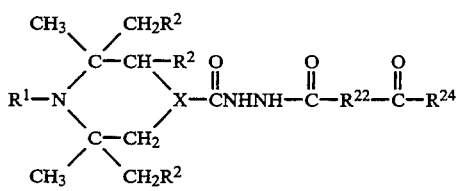

where $R^1$, $R^2$, $R^{22}$, $R^{24}$ (defined as —NH—$R^{18}$ in this case) and X are as previously defined.

The reactions are normally carried out in refluxing alcohol (i.e. methanol) but may be carried out in higher boiling aprotic solvents or without solvent by heating a mixture of the two components above their melting points. The methyl and ethyl esters of N-substituted oxamates and succinamates are the preferred coreactants.

The novel acyl derivatives of the hydrazide may be prepared by reacting the esters (cited in the literature, as above) with acid hydrazides in refluxing alcohol (i.e. methanol).

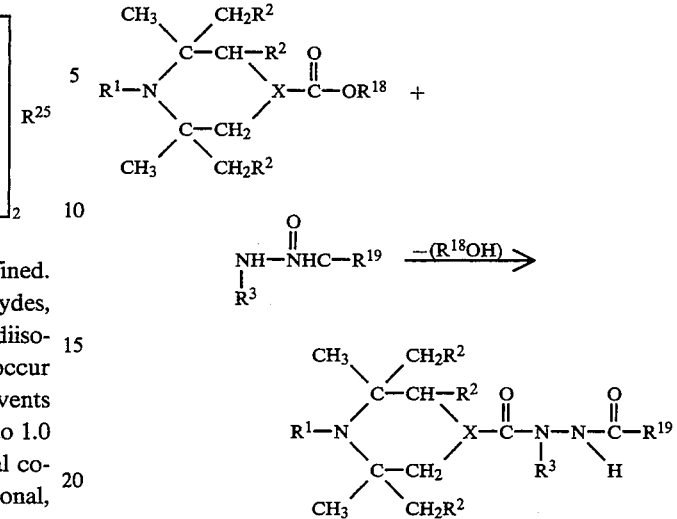

where $R^{18}$, $R^1$, $R^2$, $R^3$, $R^{19}$ and X are as previously defined.

The novel acyl derivatives may also be prepared by reacting the hydrazides with non-cyclic carboxylic acid anhydrides:

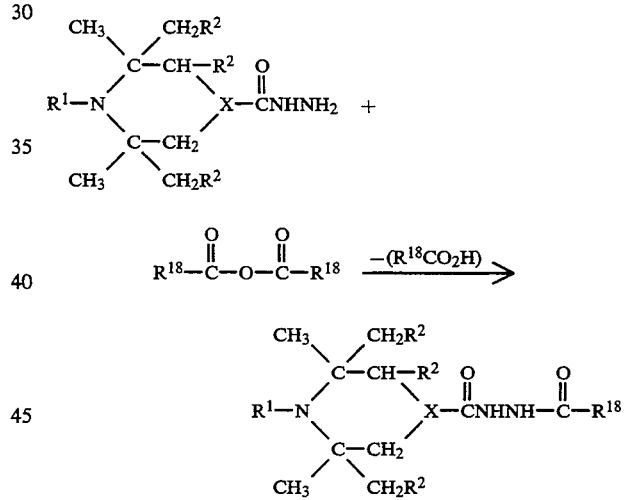

where $R^1$, $R^2$, $R^{18}$ and X are as previously defined. The reactions are typically conducted in aprotic solvents, such as tetrahydrofuran, diethyl ether or t-butyl methyl ether. However, the reaction may also be carried out by adding the anhydride to a methanolic solution of the hydrazide. In addition, when $R^1$ is hydrogen, alkyl, cycloalkyl, aralkyl or aryl, the carboxylic acid generated in the reaction may form a salt with the hindered amine. The free base derivatives may be regenerated from the carboxylic acid salt by neutralizing the salt with a stronger base than the hindered amine, for example, dilute sodium hydroxide, dilute potassium hydroxide, hydrazine or more basic amines, such as diethylamine or triethylamine.

The corresponding diacyl derivatives can be prepared by reacting the esters with diacid dihydrazides in a 2 to 1 mole ratio in refluxing alcohol (i.e. methanol).

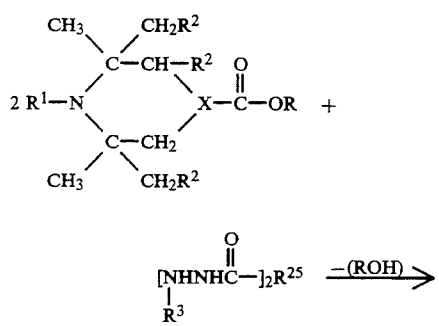

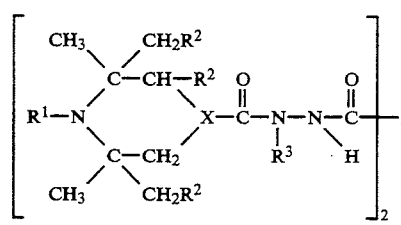

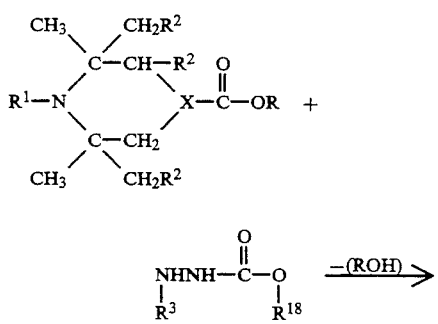

where R, $R^1$, $R^2$, $R^3$, $R^{25}$ and X are as previously defined.

The novel alkoxycarbonyl, cycloalkoxycarbonyl, aryloxycarbonyl and aralkoxycarbonyl derivatives of the hdyrazides may be prepared by reacting the ester (as described above) with the corresponding alkyl, cycloalkyl, aryl or aralkyl carbazates in refluxing alcohol (i.e. methanol).

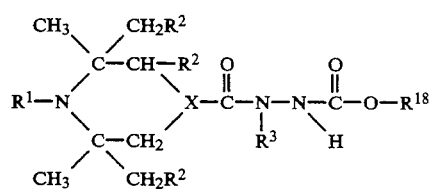

where R, $R^1$, $R^2$, $R^3$, $R^{18}$ and X are as previously defined.

Alternately, these derivatives may be prepared by reacting the hydrazide with a disubstituted carbonate or substituted haloformate. When a haloformate is used, an additional base may be used to react with the halogen acid formed. The amine group in the molecule may serve this purpose, but must then be released from its salt form by subsequent reaction with a strong base (as during workup).

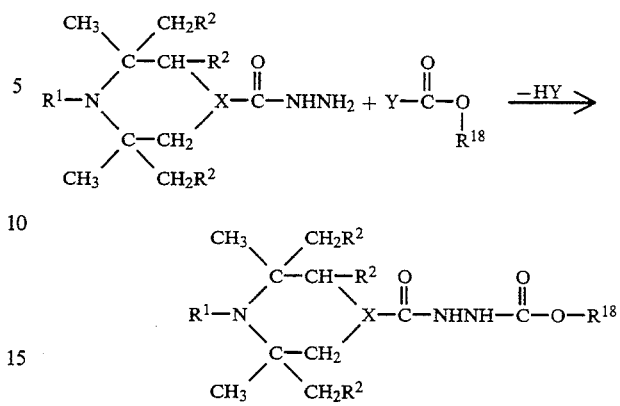

where $R^1$, $R^2$, $R^{18}$ and X are as previously defined and Y is aryloxy or halogen.

The novel dialkoxycarbonyl, dicycloalkoxycarbonyl, diaryloxycarbonyl and diaralkoxycarbonyl derivatives of the hydrazide may be prepared by reacting the esters of the literature with the corresponding biscarbazates.

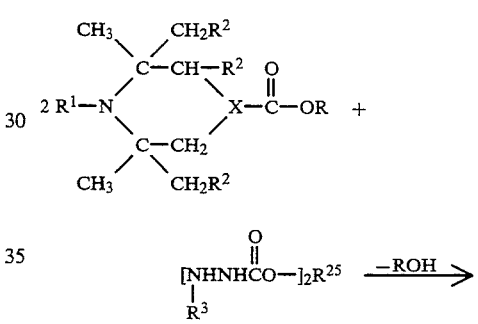

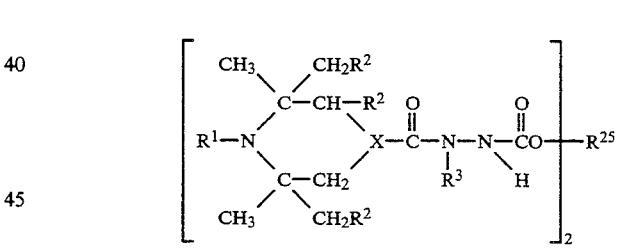

where R, $R^1$, $R^2$, $R^3$, $R^{25}$ and X are as previously defined.

The novel sulfonyl derivatives of the hydrazide may be prepared by reacting the esters of the literature with the corresponding sulfonyl hydrazide or bis(sulfonyl hydrazides).

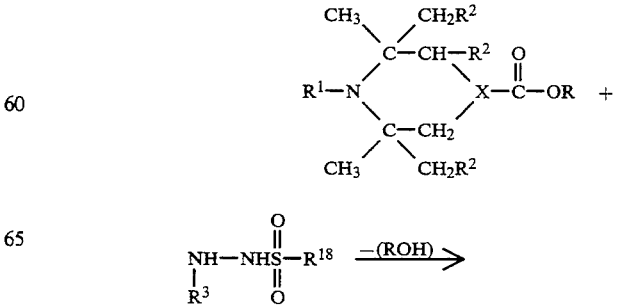

-continued

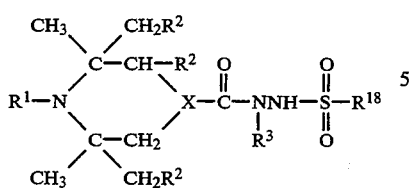

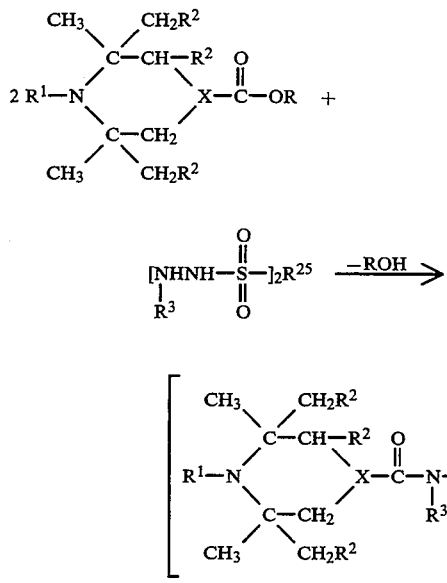

where $R^1$, $R^2$, $R^3$, $R^{18}$, $R^{25}$ and X are as previously defined.

The novel alkyl derivatives of the hydrazide may be prepared by reacting the hydrazides with epoxides. The reactions are generally carried out neat or in a minimum amount of a high boiling solvent. Reaction generally occurs quite readily at 140°–150° C.

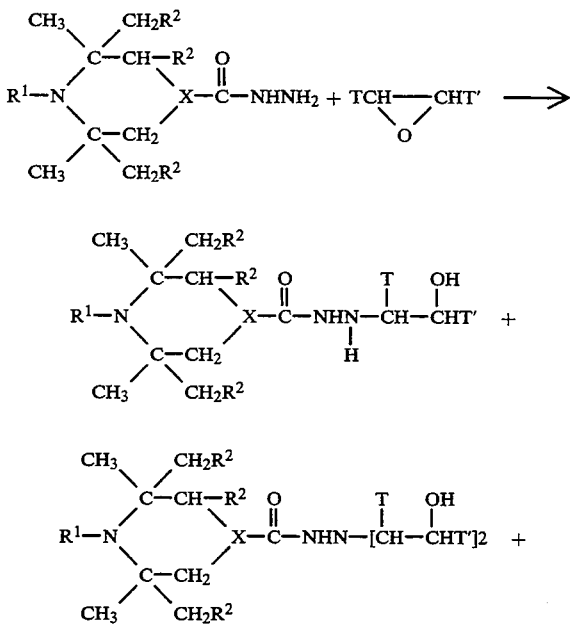

-continued

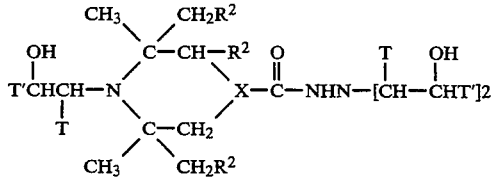

(only when $R^1$ is hydrogen)

where $R^1$, $R^2$ and X are as previously defined and T and T′ are selected from groups necessary to conform to the definitions of $R^{18}$, $R^{17}$ and $R^1$ (when applicable).

The hydrazide group reacts with two equivalents of epoxide. If the hindered amine is not substituted, it will also react with the epoxide to give a trialkylated product. The ratio of the unsubstituted hydrazide to the monoalkylated, dialkylated and trialkylated products is dependent upon the mole ratio of epoxide to hydrazide, the temperature and the concentration if the reaction is run in a solvent.

Examples of suitable ketones include acetone, methyl ethyl ketone, 2-pentanone, 2-hexanone, 3-hexanone, 2-decanone, 3-methyl-2-pentanone, 4-methyl-2-pentanone, 4-methoxy-4-methyl-2-pentanone, cyclopentanone, cyclohexanone, 2,4-dimethyl-4-heptanone, 3,5-dimethyl-4-heptanone, 2,4-dimethyl-3-pentanone, 1,3-diphenylacetone, 2-octanone, 3-octanone, dihydroisophorone, 4-t-butylcyclohexanone, methyl cyclohexyl ketone, acetophenone, 2,2,6,6-tetramethyl-4-piperidone, and 2,6-diethyl-2,3,6-trimethyl-4-piperidone.

Examples of suitable aldehydes include formaldehyde, acetaldehyde, butyraldehyde, dodecyl aldehyde, 2-ethylbutyraldehyde, heptaldehyde, isobutyraldehyde, isovaleraldehyde, octyl aldehyde, propionaldehyde, benzaldehyde, 3,5-di-t-butyl-4-hydroxybenzaldehyde, 2,3-dimethyl-p-anisaldehyde, 3-hydroxybenzaldehyde, 1-naphthaldehyde, salicylaldehyde, p-tolualdehyde and 2,3,4-trimethoxybenzaldehyde.

Examples of suitable isocyanates include allyl isocyanate, benzyl isocyanate, n-butyl isocyanate, sec-butyl isocyanate, isobutyl isocyanate, t-butyl isocyanate, cyclohexyl isocyanate, ethyl isocyanate, isopropyl isocyanate, 4-methoxyphenyl isocyanate, methyl isocyanate, octadecyl isocyanate, 1-naphthyl isocyanate, phenyl isocyanate, o-tolyl isocyanate, m-tolyl isocyanate and p-tolyl isocyanate, dimethyl-m-isopropenylbenzyl isocyanate and 2-isocyanatoethyl methacrylate.

Examples of suitable isothiocyanates include allyl isothiocyanate, benzyl isothiocyanate, 4-bromophenyl isothiocyanate, n-butyl isothiocyanate, sec-butyl isothiocyanate, isobutyl isothiocyanate, t-butyl isothiocyanate, 3-chlorophenyl isothiocyanate, cyclohexyl isothiocyanate, ethyl isothiocyanate, methyl isothiocyanate, propyl isothiocyanate, isopropyl isothiocyanate, 1-naphthyl isothiocyanate, t-octyl isothiocyanate, phenethyl isothiocyanate, phenyl isothiocyanate, propyl isothiocyanate, o-tolyl isothiocyanate, m-tolyl isthiocyanate and p-tolyl isothiocyanates.

Examples of suitable diisocyanates include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3-diisocyanate and cyclohexane-1,4-diisocyanate and mixtures thereof, 1-isocyanato-3,3,5-trimethyl-5-(isocyanatomethyl)cyclohexane (isophorone diisocyanate), 2,4-hexahydrotoluene diisocyanate and 2,6-hexahydrotoluene diisocyanate and mixtures thereof, hexahydro-1,3-phenylene diisocyanate and hexahydro-1,4-phenylene diisocyanate and mixtures thereof, 3,3'-dimethoxybiphenyl-4,4'-diisocyanate, 3,3'-dimethylbiphenyl-4,4'-diisocyanate, perhydro-2,4'-diphenylmethane diisocyanate and perhydro-4,4'-diphenylmethane diisocyanate and mixtures thereof, 1,3-phenylene diisocyanate and 1,4-phenylene diisocyanate and mixtures thereof, 2,4-tolylene diisocyanate and 2,6-tolylene diisocyanate and mixtures thereof, diphenylmethane-2,4'-diisocyanate and diphenylmethane-4,4'-diisocyanate and mixtures thereof, naphthylene-1,5-diisocyanate, m-di(2-methyl-2-isocyanatoethyl)benzene and p-di(2-methyl-2-isocyanatoethyl)benzene and mixtures thereof, 2,2,4-trimethylhexamethylene diisocyanate and 2,4,4-trimethylhexamethylene diisocyanate.

Examples of suitable diisothiocyanates include ethylene diisothiocyanate, 1,4-tetramethylene diisothiocyanate, 1,6-hexamethylene diisothiocyanate, 1,4-di(isothiocyanato)benzene, 1,1'-methylenebis(4-isothiocyanatocyclohexane) and 1,1'-oxybis(4-isothiocyanatobenzene).

Examples of suitable amic acid esters include methyl oxamate, ethyl oxamate, propyl oxamate, isopropyl oxamate, n-butyl oxamate, phenyl oxamate, methyl succinamates, ethyl succinamate, propyl succinamate, isopropyl succinamate, n-butyl succinamate, phenyl succinamate, ethyl N-(2,2,6,6-tetramethyl-4-piperidinyl)oxamate, methyl N-(2,2,6,6-tetramethyl-4-piperidinyl)oxamate, ethyl N-(2,2,6,6-tetramethyl-4-piperidinyl)succinamate, methyl N-(2,2,6,6-tetramethyl-4-piperidinyl)succinamate, ethyl N-(3,5-di-t-butyl-4-hydroxyphenyl)oxamate, methyl N-(3,5-di-t-butyl-4-hydroxyphenyl)oxamate, ethyl N-(3,5-di-t-butyl-4-hydroxyphenyl)succinamate and methyl N-(3,5-di-t-butyl-4-hydroxyphenyl)succinamate.

Examples of suitable acid hydrazides include acetyl hydrazide, propionic hydrazide, butyric hydrazide, isobutyric hydrazide, valeric hydrazide, isovaleric hydrazide, caproic hydrazide, decanoic hydrazide, lauric hydrazide, stearic hydrazide, benzhydrazide, 3,5-di-t-butyl-4-hydroxybenzhydrazide, 3-(3,5-di-t-butyl-4-hydroxyphenyl)propionic acid hydrazide, 3-(n-hexylthio)propionic acid hydrazide, (4-benzoyl-3-hydroxyphenoxy)acetyl hydrazide, and 3-(dimethylaminoethylthio)propionic acid hydrazide.

Examples of suitable diacid dihydrazides include succinic acid hydrazide, adipic acid dihydrazide, azelaic acid dihydrazide, dodecanedioic acid dihydrazide and 1,3-benzenedicarboxylic acid dihydrazide and 1,4-benzenedicarboxylic acid dihydrazide.

Examples of suitable carbazates include ethyl carbazate, methyl carbazate, propyl carbazate, isopropyl carbazate, butyl carbazate, cyclohexyl carbazate, cyclopentyl carbazate, cyclododecyl carbazate, phenyl carbazate, benzyl carbazate, 4-t-butylcyclohexyl carbazate, 2-ethylhexyl carbazate, 4-methylphenyl carbazate and 3-methoxyphenyl carbazate.

Examples of bis(carbazates) include ethylenebis(carbazate), cyclohexane-1,2-diylbis(carbazate), cyclohexane-1,4-diylbis(carbazate), decane-1,10-diylbis(carbazate), 2,2-diethylpropane-1,3-diylbis(carbazate), 2,2-dimethyl-1,3-diylbis(carbazate), hexane-1,6-diylbis(carbazate) and propane-1,3-diylbis(carbazate).

Examples of suitable diaryl carbonates include diphenyl carbonate, di-(4-methylphenyl) carbonate, di-(3-methylphenyl) carbonate, di-(3-methoxyphenyl) carbonate, di-(2,6-dimethylphenyl) carbonate and di-(2,5-di-t-butylphenyl) carbonate.

Examples of suitable sulfonyl halides include benzenesulfonyl hydrazide, 4-bromobenzenesulfonyl hydrazide, 1-butanesulfonyl hydrazide, 4-t-butylbenzenesulfonyl hydrazide, p-toluenesulfonyl hydrazide, ethanesulfonyl hydrazide, methanesulfonyl hydrazide, 4-fluorobenzenesulfonyl hydrazide, 1-hexadecanesulfonyl hydrazide, isopropanesulfonyl hydrazide and 1-naphthalenesulfonyl hydrazide.

Examples of suitable bis(sulfonyl hydrazides) include 1,3-benzenebis(sulfonyl hydrazide), 1,4-benzenebis(sulfonyl hydrazide), 1,2-ethanebis(sulfonyl hydrazide), 1,4-butanebis(sulfonyl hydrazide), 1,1'-oxybis(benzenesulfonyl hydrazide), 1,1'-methylenebis(benzenesulfonyl hydrazide) and 1,4-cyclohexanebis(sulfonyl hydrazide).

Examples of suitable epoxides include 1,2-epoxybutane, 2,3-epoxybutane, 1,2-epoxycyclododecane, 1,2-epoxycyclohexane, 1,2-epoxyoctane, 1,2-epoxydecane, 1,2-epoxydodecane, 1,2-epoxyoctadecane, 1,2-epoxy-3-phenoxypropane, 2,3-epoxypropyl acrylate, 2,3-epoxypropyl methacrylate, 2,3-epoxypropyl 4-methoxyphenyl ether, glycidyl isopropyl ether, glycidyl n-hexyl ether, glycidyl dodecyl ether and glycidyl octadecyl ether.

The following examples are presented to further illustrate the best mode contemplated by the inventor for practicing the present invention and are intended as illustrations and not as limitations of the invention.

EXAMPLE 1

20-(3-hydrazino-3-oxopropyl)-2,2,4,4-tetramethyl-7-oxa-3,20-diazadispiro[5.1.11.2]heneicosane-21-one 20-(3-Dodecyloxy-3-oxopropyl)-2,2,4,4-tetramethyl-7-oxa-3,20-diazadispiro[5.1.11.2]heneicosane-21-one (Sanduvor 3050 TM), 66.5 g (0.11 mole) was placed in a flask and dissolved with 150 ml methanol. To this was added 35 ml of hydrazine (54% in water) producing an immediate white precipitate. The mixture was stirred at ambient temperature for 28 hours. Most of the solvent was stripped using aspirator vacuum and the residue taken up in 100 ml methyl t-butyl ether and 175 ml tetrahydrofuran. The aqueous layer which separated was removed and the organic phase washed with three 50 ml portions of saturated sodium chloride. The organic material was dried with anhydrous magnesium sulfate, and the solvent was stripped using aspirator vacuum. The white semi-solid residue was slurried with pentane and isolated. The product weighed 39.4 g (79% of theory) and had two melting points at 171°–174° C. and 185° C. The infrared spectrum (in chloroform) showed a carbonyl band at 1680 cm$^{-1}$.

EXAMPLE 2

20-[5-(2,2,6,6-tetramethylpiperidine-4-ylidene)-4,5-diaza-oxopentyl]-2,2,4,4-tetramethyl-7-oxa-3,20-diazadi-spiro[5.1.11.2]heneicosane-21-one The hydrazide of Example 1, 2.25 g (0.005 mole), 2,2,6,6-tetramethyl-4-piperidone monohydrate, 0.85 g (0.005 mole), p-toluenesulfonic acid, 0.08 g, and 100 ml xylenes were combined in a flask fitted with a Dean Stark water separation assembly. The reaction mixture was heated to reflux for 3 hours with azeotropic removal of water as it formed. The mixture was cooled and transferred to a separatory funnel and washed with 25 ml 5% sodium bicarbonate. The organic material was isolated and stripped of solvent using aspirator vacuum yielding a tan residue. Analysis showed residual starting hydrazide was present. The product was put back in a flask with 2,2,6,6-tetramethyl-4-piperidone monohydrate, 0.42 g, p-toluenesulfonic acid, 0.05 g, and 100 ml xylenes. This mixture was heated to reflux for an hour with water removal. The reaction mixture was cooled and transferred to a separatory funnel, washed with 25 ml 5% sodium bicarbonate and the solvent stripped using aspirator vacuum. The residue was recrystallized from toluene yielding 1.9 g of white crystals (66% of theory), melting 142°–144° C. The infrared spectrum (in chloroform) showed a single broad carbonyl band at 1685 cm$^{-1}$. The mass spectrum showed the molecular ion at m/e 588.

EXAMPLE 3

20-[5-(3,3,5-trimethylcyclohexylidene)-4,5-diaza-3-oxopentyl]-2,2,4,4-tetramethyl-7-oxa-3,20-diazadispiro[5.1.11.2]heneicosane-21-one The hydrazide of Example 1, 2.25 g (0.005 mole), 3,3,5-trimethylcyclohexanone, 0.7 g (0.005 mole) and 100 ml xylenes were combined in a flask fitted with a Dean Stark water separation assembly. The reaction mixture was heated to reflux for 2 hours with azeotropic removal of water as it formed. At this time, additional trimethylcyclohexanone, 0.35 g was added and the reaction continued for 30 minutes. The mixture was cooled and stripped of solvent using aspirator vacuum yielding 2.9 g of tan crystals (99% of theory), melting 190°–193° C. The infrared spectrum (in chloroform) showed a single broad carbonyl at 1680 cm$^{-1}$. The mass spectrum showed the molecular ion at m/e 573.

EXAMPLE 4

20-[4,5,7-triaza-3,6-dioxopentacosyl]-2,2,4,4-tetramethyl-7-oxa-3,20-diazadi-spiro[5.1.11.2]heneicosane-21-one The hydrazide of Example 1, 2.25 g (0.005 mole), octadecyl-isocyanate, 1.48 g (0.005 mole) and 100 ml tetrahydrofuran were combined in a flask under nitrogen atmosphere. The reaction mixture was heated to reflux for 1 hour. The mixture was cooled and stripped of solvent using aspirator and high vacuum yielding 3.8 g of gummy solid (100% of theory), which turned to white crystals upon cooling with dry ice. The melting range was 40°–45° C. The infrared spectrum (in chloroform) showed a single broad carbonyl band at 1685 cm$^{-1}$. The mass spectrum showed the molecular ion at m/e 746.

EXAMPLE 5

20-[8-(2,2,6,6-tetramethyl-4-piperidinyl)-4,5,8-triaza-3,6,7-trioxooctyl]-2,2,4,4-tetramethyl-7-oxa-3,20-diazadispiro[5.1.11.2]heneicosane-21-one The hydrazide of Example 1, 2.25 g (0.005 mole), ethyl2-(2,2,6,6-tetramethyl-4-piperidinylamino)-2-oxoacetate, 2.09 g (0.005 mole) and 50 ml methanol were combined in a flask fitted with a distillation head. The mixture was heated to reflux and the solvent slowly distilled, removing about 40 ml over 5.5 hours producing a thick paste. Distillation ceased for an additional 5 hours reflux. The reaction mixture was cooled and the solid isolated by filtration, using additional methanol to rinse the solids. The filtrate was put back in the reaction flask and heated to reflux distilling all but about 5 ml solvent over a 3 hour period, forming and precipitating addition product. The reaction was again cooled, and the solid isolated. The solids were combined and dissolved in 100 ml hot tetrahydrofuran and the hot solution filtered. The solvent was stripped using aspirator and high vacuum to give 1.9 g of white crystals (58% of theory) melting 130°–135° C. The infrared spectrum (in chloroform) showed two carbonyl bands at 1665 and 1685 cm$^{-1}$. The mass spectrum showed the molecular ion at m/e 661.

EXAMPLE 6

20-[4,5-diaza-3,6-dioxo-9-ethyl-7-oxatridecyl]-2,2,4,4-tetramethyl-7-oxa-3,20-diazadispiro[5.1.11.2]heneicosane-21-one The hydrazide of Example 1, 2.25 g (0.005 mole), was slurried in 35 ml tetrahydrofuran and 2-ethylhexyl chloroformate, 0.96 g (0.005 mole) was added at ambient temperature producing an exotherm to 35° C. and dissolving the hydrazide. The mixture was heated to reflux for 1 hour. The reaction mixture was cooled and transferred to a separatory funnel with 100 ml methyl t-butyl ether. The organic mixture was washed with three 50 ml portions of 10% sodium carbonate and two 50 ml portions water. The organic material was dried using anhydrous magnesium sulfate and the solvent stripped using aspirator and high vacuum. The residue was 3.0 g of white crystals (100% of theory) melting 65°–68° C. The infrared spectrum (in chloroform) showed two carbonyl bands at 1685 and 1750 cm$^{-1}$. The mass spectrum showed the molecular ion at m/e 607.

EXAMPLE 7

20-(8-carboxy-4,5-diaza-3,6-dioxoheptacosyl)-2,2,4,4-tetramethyl-7-oxa-3,20-diazadispiro[5.1.11.2]heneicosane-21-one The hydrazide of Example 1, 4.52 g (0.01 mole), octadecylsuccinic anhydride, 3.50 g (0.01 mole) and 50 ml tetrahydrofuran were combined and refluxed for 45 minutes. The solution was cooled and stripped of solvent using aspirator and high vacuum. A white solid was obtained. The infrared spectrum (KBr) showed a broad carbonyl band over the range 1620–1710 cm$^{-1}$ and a broad OH band 2900–3300 cm$^{-1}$.

EXAMPLE 8

20-{3-[N-(octadecylsuccinimido)amino]-3-oxopropyl}-2,2,4,4-tetramethyl-7-oxa-3,20-diazadispiro[5.1.11.2]heneicosane-21-one The hydrazide of Example 7 and 100 ml xylenes were combined in a flask fitted with a Dean Stark water separation assembly. The reaction mixture was heated to reflux for 3 hours with azeotropic removal of water as it formed. The xylenes were stripped using aspirator vacuum and the residual oil was mixed with 100 ml acetone which quickly solidified the oil. The solid was filtered and dried for 1 hour on the filter funnel. The white solid product weighed 4.8 g and had a melting range of 105°–110° C. The infrared spectrum (in chloroform) showed two carbonyl bands at 1675 and 1730 cm$^{-1}$. The OH band of the starting amic acid was not observed.

EXAMPLE 9

20-{3-[N-(4-methylhexahydrophthalimido)amino]-3-oxopropyl}-2,2,4,4-tetramethyl-7-oxa-3,20-diazadispiro[5.1.11.2]heneicosane-21-one The hydrazide of Example 1, 13.5 g (0.03 mole), was added to 225 ml xylene at 75° C. Added dropwise to this was 4-methylhexahydrophthalic anhydride, 5.1 g (0.03 mole) in 25 ml xylene. The apparatus was fitted with a Dean Stark water separation assembly and the reaction mixture was heated to reflux for 4 hours with azeotropic removal of water as it formed. The xylenes were stripped using aspirator vacuum and the residual sticky solid was slurried with 300 ml pentane. The solid was filtered and dried for 2 hours on the filter funnel. The white solid product weighed 11.7 g and had a melting range of 210°-212° C. The infrared spectrum (mull) showed two carbonyl bands at 1690 and 1730 cm$^{-1}$.

EXAMPLE 10

20-[4,5,7-triaza-3,6-dioxoundecyl]-2,2,4,4-tetramethyl-7-oxa-3,20-diazadispiro[5.1.11.2]heneicosane-21-one The hydrazide of Example I, 5.4 g (0.012 mole), butylisocyanate, 1.2 g (0.012 mole), and 50 ml tetrahydrofuran were combined and heated to reflux for 1.5 hours. The mixture was cooled and the precipitated product was filtered and air dried for 4 hours. The product weighed 5.1 g (77% of theory) and had melting range 58°-63° C.

EXAMPLE 11

3-(Hydrazinocarbonylmethyl)-7,7,9,9-tetramethyl-1,3,8-triazaspiro[4.5]decane-2,4-dione A. Ethyl bromoacetate (1.9 g, 0.011 mole), the potassium salt of 7,7,9,9-tetramethyl-1,3,8-triazaspiro[4.5]-decane-2,4-dione (2.6 g, 0.010 mole) and 30 ml of dimethylformamide were combined in a flask under nitrogen. The mixture was heated to 60° C. for 2.5 hours. The solvent was stripped leaving a solid residue which was dissolved in 100 ml methylene chloride. The solution was washed with 100 ml of water. The organic solution was dried with anhydrous magnesium sulfate and the solvent removed under vacuum to give 2.2 g of white solid with melting range 134°-136° C. The infrared spectrum of the product had three carbonyl absorption bands at 1715 cm$^{-1}$, 1750 cm$^{-1}$ and 1780 cm$^{-1}$. Additional confirmation of product integrity was obtained from the NMR spectrum.

B. The ester prepared above (1.2 g, 0.004 mole) was dissolved in 50 ml methanol. To this was added 54% hydrazine (5 ml) and the resulting solution was stirred for 4 hours. The solvent was removed under vacuum to yield a gum which was slurried with 50 ml tetrahydrofuran and this solvent stripped under vacuum to give 1.1 g white solid. This solid as dissolved in methylene chloride and filtered. The solvent was removed under vacuum to give 0.8 g white solid have melting range 75°-85° C. The infrared spectrum had two carbonyl absorptions at 1720 cm$^{-1}$ and 1780 cm$^{-1}$. Additional confirmation of product integrity was obtained from the NMR spectrum and the mass spectrum showed the molecular ion at m/e 298.

EXAMPLE 12

3-(Hydrazinocarbonylmethyl)-7,7,9,9-tetramethyl-1,3,8-triazaspiro[4.5]decane-2,4-dione, acetophenone hydrazone The hydrazide of example 10 (2.0 g, 0.007 mole) and acetophenone (0.8 g, 0.007 mole) were combined in 100 ml xylenes in a flask equipped with a Dean Stark water separation assembly. The solution was heated to reflux for 2 hours before the addition of p-toluenesulfonic acid monohydrate (0.07 g). Reflux was continued for 54 hours with azeotropic removal of water. Additional acetophenone (0.8 g) was added and reflux continued for a total of 76 hours. The solvent and residual acetophenone were removed under vacuum with heating to 180° C. to give 2.4 g of slightly yellow solid having melting range 215°-225° C. The infrared spectrum of the product showed merged carbonyl absorptions with peak at 1722 cm$^{-1}$.

EXAMPLE 13

Evaluation of Tensile Bars Containing HALS Hydrazides or Derivatives

Dry blends of Himont 6501 polypropylene, the HALS stabilizer and optionally a small amount of a hindered phenol antioxidant (Irganox 1076, product of Ciba-Geigy) and/or UV absorber (UV-Check AM-340, product of Ferro Corp) were prepared in a polyethylene container as specified in Table I. The blends were shaken well to insure a good dispersion of the additive in the polypropylene. The blends were then extruded on a Brabender Prep Center Extruder Model No. 1340 having a 1.25 inch screw diameter with a length to diameter ratio of 25:1. The extruder was operated at a screw speed of 30 RPM and all the heating zones were controlled at 200° C. The first 100 grams of extrudate were used to purge out the extruder between runs and were discarded. The remaining extrudate was air-cooled and pelletized. The concentration of the 2,2,6,6-tetramethyl-4-piperidinyl group in the polypropylene was approximately 0.3%. The concentration of the Irganox 1076, when used, was approximately 0.25%. The concentration of UV-Check AM-340, when used, was approximately 0.22%.

The pellets were injection molded in a Newbury 25 ton injection molding machine at 400° F. into 7+⅜ inch×¾ inch×⅛ inch tensile bars.

A control sample containing only Irganox 1076 was included for comparison. Control samples containing Irganox 1076 and either Chimassorb 944 (HALS product of Ciba Geigy) or Tinuvin 770 (HALS product of Ciba Geigy) were also included for comparison.

The tensile bars were placed in a QUV Accelerated Weathering Tester (Q Panel Company) for various exposure times. The QUV contained UV-B bulbs and operated with an 8 hour light cycle at 60° C. and a 4 hour condensation cycle at 50° C. Samples were withdrawn periodically at the same time of day. The tensile bars were pulled on an instrumented Instron according to ASTM Procedure 638. The minimum QUV exposure time required to obtain a brittle break in the Instron was determined. A result was considered a brittle break when the tensile bar snapped before 15% elongation was obtained.

The QUV time interval required to generate spotting and clouding of the surface of the tensile bars was also noted.

The results indicate that the compounds of this invention are efficient light stabilizers for polypropylene and in most cases are considerably more efficient than the commercial light stabilizers against UV-B light.

TABLE I

| | Light Stabilizer in Polypropylene Test Formulations | | | | | | |
|---|---|---|---|---|---|---|---|
| Form. No. | HALS Additive | HALS g | PP g | Irg 1076* g | UV-C AM-340+ g | Days To Spotting | Days To Brittle Break |
| I | Hydrazide of Ex 1 | 4.3 | 445 | 0 | 0 | 31–34 | 21–30 |
| II | Hydrazide of Ex 1 | 4.3 | 445 | 1.1 | 0 | 41–49 | 26–30 |
| III | Hydrazide of Ex 9 | 5.7 | 445 | 0 | 0 | <20 | <11 |
| IV | Hydrazide of Ex 9 | 5.7 | 445 | 1.1 | 0 | 31–34 | 20–25 |
| V | Hydrazide of Ex 6 | 5.9 | 445 | 1.1 | 0 | 50–60 | 20–25 |
| VI | Hydrazide of Ex 6 | 5.9 | 445 | 1.2 | 1.2 | 0 | >60 |
| VII | Hydrazide of Ex 10 | 5.2 | 445 | 0 | 0 | >35 | 18–20 |
| — | None | | 445 | 1.1 | 0 | — | <5 |
| — | Chimassorb 944 | | 445 | 1.1 | 0 | 33 | 21–24 |
| — | Tinuvin 770 | | 445 | 1.1 | 0 | >35 | 21–24 |

*Irganox 1076, a product of Ciba Geigy
+UV-Check AM-340, a product of Ferro Corp

I claim:
1. A process for stabilizing a synthetic or natural polymer composition against the degradative effects of heat and light which comprises incorporating into a composition comprising at least one natural or synthetic polymer a stabilizing effective amount of a hindered amine compound of the formula

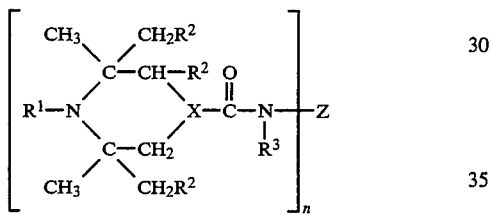

where
$R^1$ is hydrogen, oxyl, hydroxyl, substituted or unsubstituted aliphatic of 1–20 carbons, substituted or unsubstituted alicyclic of 5–12 carbons, substituted or unsubstituted carbocyclic araliphatic of 7–22 carbons, substituted or unsubstituted aliphatic acyl of 2–20 carbons, substituted or unsubstituted alicyclic acyl of 7–16 carbons, substituted or unsubstituted carbocyclic aromatic acyl of 7–11 carbons, substituted or unsubstituted carbocyclic araliphatic acyl of 7–22 carbons, —(C(=O))$_a$—N(R$^4$)(R$^5$), —(C(=O))$_a$—O—R$^6$, —(CH$_2$)$_a$—C(=O)—O—R$^7$ where a is 1–2, or —(CH$_2$—CH(R$^8$)—O)$_b$—R$^9$ where b is 2–50;
$R^2$ is hydrogen or aliphatic of 1–4 carbons;
$R^3$ is hydrogen, substituted or unsubstituted aliphatic of 1–20 carbons, substituted or unsubstituted carbocyclic araliphatic of 7–22 carbons or substituted or unsubstituted alicyclic of 5–12 carbons;
$R^4$ and $R^5$ are independently hydrogen, substituted or unsubstituted aliphatic of 1–20 carbons, substituted or unsubstituted carbocyclic aryl of 6–14 carbons, substituted or unsubstituted carbocyclic araliphatic of 7–22 carbons or substituted or unsubstituted alicyclic of 5–12 carbons which may optionally contain —N(R$^{10}$)— as a ring member with the proviso that bonding to the amide nitrogen to which R$^4$ and R5 are attached is through a carbon atom, or R$^4$ and R$^5$ may be linked together through —N(R$^{10}$)— or —O— to form a heterocyclic ring including the nitrogen atom to which they are attached of 5–7 atoms with the proviso that the —N(R$^{10}$)— or —O— linking R$^4$ and R$^5$ must be separated from the nitrogen atom to which R$^4$ and R$^5$ are attached by at least one carbon atom;

$R^6$ is substituted or unsubstituted aliphatic of 1–20 carbons, substituted or unsubstituted alicyclic of 5–12 carbons, substituted or unsubstituted carbocyclic aryl of 6–14 carbons or substituted or unsubstituted carbocyclic araliphatic of 7–22 carbons, $R^7$, $R^8$ and $R^9$ are independently hydrogen, substituted or unsubstituted aliphatic of 1–20 carbons, substituted or unsubstituted alicyclic of 5–12 carbons, substituted or unsubstituted carbocyclic aryl of 6–14 carbons or substituted or unsubstituted carbocyclic araliphatic of 7–22 carbons, $R^{10}$ is hydrogen, substituted or unsubstituted aliphatic of 1–20 carbons, substituted or unsubstituted alicyclic of 5–12 carbons, substituted or unsubstituted carbocyclic araliphatic of 7–22 carbons, substituted or unsubstituted aliphatic acyl of 2–20 carbons, substituted or unsubstituted alicyclic acyl of 7–16 carbons, substituted or unsubstituted carbocyclic aromatic acyl of 7–11 carbons, substituted or unsubstituted carbocyclic araliphatic acyl of 7–22 carbons, —(C(=O))$_a$—N(R$^4$)(R$^5$), —(C(=O))$_a$—O—R$^6$, —(CH$_2$)$_a$—C(=O)—O—R$^7$ where a is 1–2, or —(CH$_2$—CH(R$^8$)—O)$_b$—R$^9$ where b is 2–50, X is a triradical

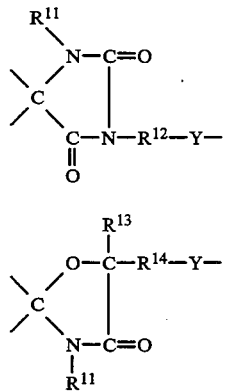

-continued

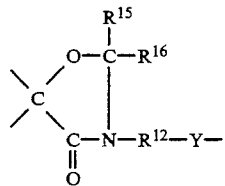

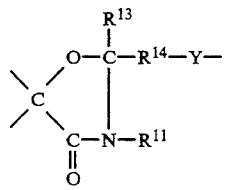

or

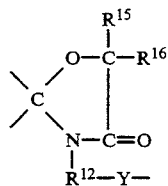
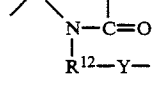

$R^{11}$ is independently of the same definition as $R^7$ and when alicyclic may optionally contain —N($R^{10}$)— as a ring member, with the proviso that bonding to the nitrogen atom to which "R" is attached must be through a carbon atom;

$R^{12}$ is substituted or unsubstituted aliphatic diradical of 1–20 carbons, substituted or unsubstituted carbocyclic aryl diradical of 6–12 carbons, substituted or unsubstituted alicyclic diradical of 5–12 carbons or substituted and unsubstituted carbocyclic araliphatic diradical of 7–22 carbons and the diradicals may optionally contain 1–6 heteroatoms —O—, —S—, and —N($R^{10}$)— with the proviso that multiple heteroatoms must be separated from each other by at least two carbon atoms and from the diradical ends by at least one carbon atom;

$R^{13}$ is independently of the same definition as $R^6$;

$R^{14}$ is independently of the same definition as $R^{12}$, and when Y is a direct bond, $R^{14}$ may also be a direct bond;

$R^{13}$ and $R^{14}$ together with the carbon atom linking them may form a substituted or unsubstituted cycloalkyl ring of 5–12 carbons, $R^{15}$ and $R^{16}$ are independently of the same definition as $R^{11}$ and may also be carbamoyl, alkoxycarbonyl of 2–5 carbons or pyridyl, and $R^{15}$ and $R^{16}$ may be linked together to form an alicyclic of 5–12 carbons, or may be linked together through a heteroatom —O—, —S—, and —N($R^{10}$)— to form a heterocyclic ring including the carbon atom to which they are attached of 5–7 atoms with the proviso that multiple heteroatoms must be separated from each other by at least two carbon atoms;

Y is —O—, —N($R^{11}$)— or a direct bond;

n is 1 or 2;

when n is 1, Z is

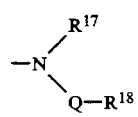

-continued

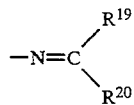

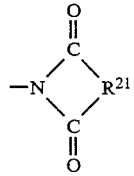

or

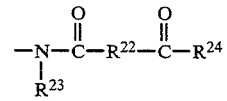

when n is 2, Z is

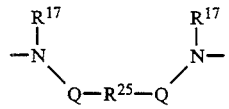

$R^{17}$ is independently of the same definition as $R^{11}$, $R^{18}$ is independently of the same definition as $R^{11}$, Q is —C(=O)—, —S(=O)$_2$—, —C(=O)—O—, —[C(=O)]$_2$—O—, —C(=O)—N($R^{10}$)—, —[C(=O)]$_2$—N($R^{10}$)—, —C(=S)—N($R^{10}$)—, —C(=O)—$R^{22}$—C(=O)—N($R^{10}$)— or, when n is 1, a direct bond between the nitrogen and $R^{18}$, $R^{19}$ and $R^{20}$ are independently of the same definition as $R^{11}$, and $R^{19}$ and $R^{20}$ may be linked together to form a substituted or unsubstituted alicyclic ring of 5–12 carbons or may be linked together through —N($R^{10}$)—, —O— and —S— to form a heterocyclic ring including the carbon atom to which they are attached of 5–12 atoms, $R^{21}$ is substituted or unsubstituted aliphatic diradical of 2–200 carbons, substituted or unsubstituted carbocyclic aryl diradical of 6–14 carbons, substituted or unsubstituted alicyclic diradical of 5–12 carbons or substituted or unsubstituted carbocyclic araliphatic diradical of 7–22 carbons, and the diradical chain(s) may optionally contain 1–6 heteroatoms —O—, —S— and —N($R^{10}$)— with the provisos that (a) multiple heteroatoms must be separated from each other by at least two carbon atoms and from the chain ends by at least one carbon atom, and that (b) the cyclic group formed contains 5–6 atoms in the ring, $R^{22}$ is a direct bond or is a substituted or unsubstituted aliphatic diradical of 1–200 carbons, substituted or unsubstituted carbocyclic aryl diradical of 6–14 carbons, substituted or unsubstituted alicyclic diradical of 5–12 carbons or substituted or unsubstituted carbocyclic araliphatic diradical of 7–22 carbons, and the diradical chain(s) may optionally contain 1–6 heteroatoms —O—, —S—, and —N($R^{10}$)— with the proviso that multiple heteroatoms must be separated from each other by at least two carbon atoms and from the chain ends by at least one carbon atom, $R^{23}$ is independently of the same definition as $R^{11}$, $R^{24}$ is chosen from —NH($R^{18}$), —OH and O⁻M⁺, where M⁺ is sodium ion, potassium ion or ammonium ion, $R^{25}$ is substituted or unsubstituted aliphatic diradical of 1–20 carbons, substituted or unsubstituted aryl diradical of 6–12 carbons, substituted or unsubstituted alicyclic diradical of 5–12 carbons or substituted or unsubstituted carbocyclic araliphatic diradical of 7–22 carbons, and the diradical chain(s) may optionally contain 1–6 moieties selected from —O— and —N($R^{10}$)— with the proviso that multiple heteroatoms must be separated from each other by at least two carbon atoms and from the chain ends by at least one carbon atom, and optional substitutents for $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{25}$ are one or more of the following: chloro, bromo, alkyl of 1–8 carbons, alkoxy of 1–12 carbons, phenoxy, cyano, hydroxy, epoxy, carboxy, benzoyl, benzoyloxy, dialkylamino of 2–8 carbons total, alkyoxycarbonyl of 2–6 carbons, acyloxy of 1–4 carbons, acryloyl, acryloyloxy, methacryloyl, methacryloyloxy, hydroxymethyl, hydroxyethyl, alkylthio of 1–4 carbons and trialkoxysilyl of 3–12 carbons; and additional optional substituents for $R^{21}$ and $R^{22}$ are alkyl of 5–180 carbons, alkylthio of 5–180 carbons, carbocyclic aralkylthio of 7–20 carbons, carbocyclic arylthio of 6–20 carbons, alkenyl of 2–180 carbons, cycloalkenyl of 5–12 carbons, carbocyclic aryl of 6–16 carbons, carbocyclic aralkyl of 7–17 carbons, carbocyclic aryloxy of 6–16 carbons, alkoxycarbonyl of 7–10 carbons, and (alkoxycarbonyl)alkylthio of 3–30 carbons; and additional substituents for $R^{18}$ are chosen from aliphatic of 1–20 carbons, cycloaliphatic of 5–12 carbons, carbocyclic aryl of 6–14 carbons, carbocyclic aralkyl of 7–22 carbons, alkoxy of 1–20 carbons, cycloalkoxy of 5–12 carbons, carbocyclic aryloxy of 6–14 carbons, carbocyclic aralkoxy of 7–15 carbons, aliphatic acyloxy of 2–20 carbons, alicyclic acyloxy of 6–13 carbons, carbocyclic aromatic acyloxy of 7–15 carbons, and carbocyclic araliphatic acyloxy of 8–16 carbons.

2. A process as defined in claim 1 wherein in the hindered amine compound:

$R^1$ is hydrogen, substituted or unsubstituted aliphatic of 1–4 carbons, substituted or unsubstituted carbocyclic araliphatic of 7–10 carbons, substituted or unsubstituted aliphatic acyl of 2–6 carbons or substituted or unsubstituted benzoyl, $R^2$ is hydrogen or methyl, $R^3$ is hydrogen, $R^4$ and $R^5$ are independently hydrogen, substituted or unsubstituted aliphatic of 1–8 carbons, substituted or unsubstituted phenyl or substituted or unsubstituted benzyl, $R^6$ is substituted or unsubstituted aliphatic of 1–8 carbons, substituted or unsubstituted phenyl or substituted or unsubstituted benzyl, $R^7$, $R^8$ and $R^9$ are independently hydrogen, substituted or unsubstituted aliphatic of 1–8 carbons, substituted or unsubstituted phenyl or substituted or unsubstituted benzyl, $R^{10}$ is hydrogen, substituted or unsubstituted aliphatic of 1–4 carbons, substituted or unsubstituted carbocyclic araliphatic of 7–10 carbons, substituted or unsubstituted aliphatic acyl of 2–6 carbons or substituted or unsubstituted benzoyl, $R^{15}$ and $R^{16}$ are independently substituted or unsubstituted aliphatic of 1–20 carbons, substituted or unsubstituted alicyclic of 5–6 carbons, substituted or unsubstituted carbocyclic aryl of 6–10 carbons, substituted or unsubstituted carbocyclic araliphatic of 7–16 carbons, or may be linked together to form an alicyclic of 5–12 carbons or may be linked together to form a group of formula

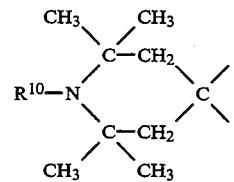

$R^{18}$ is selected from hydrogen, substituted or unsubstituted aliphatic of 1–12 carbons, substituted or unsubstituted alicyclic of 5–8 carbons, substituted or unsubstituted phenyl or substituted or unsubstituted carbocyclic araliphatic of 7–9 carbons and when alicyclic $R^{18}$ may optionally contain 1–2 moieties selected from —O— and —N($R^{10}$)— with the proviso stated in claim 1, Q is —C(=O)—, —C(=O)—O—, —[C(=O)]-2—O—, —C(=O)—N($R^{10}$)—, —[C(=O)]-2—N($R^{10}$)— or, when n is 1, a direct bond between the nitrogen and $R^{18}$, $R^{19}$ and $R^{20}$ are independently substituted or unsubstituted aliphatic of 1–8 carbons, substituted or unsubstituted alicyclic of 5–8 carbons, substituted or unsubstituted carbocyclic aryl of 6–12 carbons or substituted or unsubstituted carbocyclic araliphatic of 7–14 carbons, and $R^{19}$ and $R^{20}$ may be linked together to form a substituted or unsubstituted cycloalkyl ring of 5–8 carbons or a group of formula

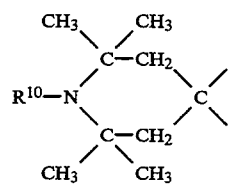

$R^{21}$ is substituted or unsubstituted aliphatic diradical of 2–18 carbons, substituted or unsubstituted orthophenylene or substituted or unsubstituted alicyclic diradical of 6–8 carbons, and the diradical chain(s) may optionally contain 1–2 moieties —O— and —N($R^{10}$)— with the proviso stated in claim 1, $R^{22}$ is substituted or unsubstituted aliphatic diradical of 2–18 carbons, substituted or unsubstituted phenylene or substituted or unsubstituted alicyclic diradical of 6–8 carbons, and the diradical chain(s) may optionally contain 1–2 moieties —O— and —N($R^{10}$)— with the proviso stated in claim 1, $R^{24}$ is —OH or —O⁻M⁺ where M is sodium ion, $R^{25}$ is substituted or unsubstituted aliphatic diradical of 2–12 carbons, substituted or unsubstituted aryl diradical of 6–12 carbons, substituted or unsubstituted alicyclic diradical of 5–12 carbons or substituted or unsubstituted araliphatic diradical of 7–12 carbons, and the diradical chain(s) may optionally contain 1-2 moieties selected from —O— and —N(R¹⁰)— with the proviso stated in claim 1.

3. A process as defined in claim 1 wherein in the hindered amine compound:
R¹ is hydrogen, methyl, acetyl or benzoyl,
R² is hydrogen,
R⁴ is hydrogen, methyl or ethyl,
R⁵ is substituted or unsubstituted aliphatic of 1-8 carbons, or substituted or unsubstituted phenyl,
R¹⁰ is hydrogen, methyl, acetyl or benzoyl,
R¹⁷ is hydrogen, substituted or unsubstituted aliphatic of 1-10 carbons, substituted or unsubstituted cyclohexyl, substituted or unsubstituted phenyl or substituted or unsubstituted carbocyclic araliphatic of 7-14 carbons,
R¹⁸ is selected from hydrogen, substituted or unsubstituted aliphatic of 1-10 carbons, substituted or unsubstituted cyclohexyl, substituted or unsubstituted phenyl or substituted or unsubstituted carbocyclic araliphatic of 7-14 carbons and when alicyclic R¹⁸ may be substituted piperidin-4-yl,
R²⁴ is —OH,
R²⁵ is substituted or unsubstituted aliphatic diradical of 2-10 carbons, substituted or unsubstituted phenylene, substituted or unsubstituted allcyclic diradical of 5-8 carbons or substituted or unsubstituted carbocyclic araliphatic diradical of 7-12 carbons.

4. A process as defined in claim 2 wherein in the hindered amine compound: R¹⁷ is hydrogen, substituted or unsubstituted aliphatic of 1-12 carbons, substituted or unsubstituted alicyclic of 5-8 carbons, substituted or unsubstituted phenyl, or substituted or unsubstituted carbocyclic araliphatic of 7-9 carbons.

5. A process as defined in claim 3 wherein the hindered amine compound is:
20-(3-hydrazino-3-oxopropyl)-2,2,4,4-tetramethyl-7-oxa-3,20-diaza-dispiro[5.1.11.2]heneicosane-21-one.

6. A process as defined in claim 3 wherein the hindered amine compound is:
20-[5-(2,2,6,6-tetramethylpiperidine-4-ylidene)-4,5-diaza-3-oxopentyl]-2,2,4,4-tetramethyl-7-oxa-3,20-diazadispiro[5.1.11.2]heneicosane-21-one.

7. A process as defined in claim 1 wherein the hindered amine compound is:
20-[5-(3,3,5-trimethylcyclohexylidene)-4,5-diaza-3-oxopentyl]-2,2,4,4-tetramethyl-7-oxa-3,20-diazadispiro[5.1.11.2]heneicosane-21-one.

8. A process as defined in claim 1 wherein the hindered amine compound is 20-[4,5,7-triaza-3,6-dioxopentacosyl]-2,2,4,4-tetramethyl-7-oxa-3,20-diazadispiro[5.1.11.2]heneicosane-21-one.

9. A process as defined in claim 3 wherein the hindered amine compound is:
20-[8-(2,2,6,6-tetramethyl-4-piperidinyl)-4,5,8-triaza-3,6,7-trioxooctyl]-2,2,4,4-tetramethyl-7-oxa-3,20-diazadispiro[5.1.11.2]heneicosane-21-one.

10. A process as defined in claim 3 wherein the hindered amine compound is:
20-[4,5-diaza-3,6-dioxo-9-ethyl-7-oxatridecyl]-2,2,4,4-tetramethyl-7-oxa-3,20-diazadispiro[5.1.11.2-]heneicosane-21-one.

11. A process as defined in claim 3 wherein the hindered amine compound is:
20-(8-carboxy-4,5-diaza-3,6-dioxoheptacosyl)-2,2,4,4-tetramethyl-7-oxa-3,20-diazadispiro[5.1.11.2-]heneicosane-21-one.

12. A process as defined in claim 3 wherein the hindered amine compound is:
20-{3-[N-(octadecyl-succinimido)amino]-3-oxopropyl}-2,2,4,4-tetramethyl-7-oxa-3,20-diazadispiro[5.1.11.2]heneicosane-21-one.

13. A process as defined in claim 3 wherein the hindered amine compound is:
20-{3-[N-(4-methyl-hexahydrophthalimido)amino]3-oxopropyl}-2,2,4,4-tetramethyl-7-oxa 3,20-diazadispiro[5.1.11.2]heneicosane-21-one.

14. A stabilized composition comprising a natural or synthetic polymer and a stabilizing effective amount of a hindered amine compound of the formula $$\left[ \begin{array}{c} CH_3 \diagdown \quad \diagup CH_2R^2 \\ C-CH-R^2 \quad O \\ R^1-N \diagup \quad \diagdown X-C-N-Z \\ \diagdown \quad \diagup \quad | \\ C-CH_2 \quad R^3 \\ CH_3 \diagup \quad \diagdown CH_2R^2 \end{array} \right]_n$$

where
R¹ is hydrogen, oxyl, hydroxyl, substituted or unsubstituted aliphatic of 1-20 carbons, substituted or unsubstituted alicyclic of 5-12 carbons, substituted or unsubstituted carbocyclic araliphatic of 7-22 carbons, substituted or unsubstituted aliphatic acyl of 2-20 carbons, substituted or unsubstituted alicyclic acyl of 7-16 carbons, substituted or unsubstituted carbocyclic aromatic acyl of 7-11 carbons, substituted or unsubstituted carbocyclic araliphatic acyl of 7-22 carbons, —(C(=O))$_a$—N(R⁴)(R⁵), —(C(=O))$_a$—O—R⁶, —(CH₂)$_a$—C(=O)—O—R⁷ where a is 1-2, or —(CH₂—CH(R⁸)—O)$_b$—R⁹ where b is 2-50;
R² is hydrogen or aliphatic of 1-4 carbons;
R³ is hydrogen, substituted or unsubstituted aliphatic of 1-20 carbons, substituted or unsubstituted carbocyclic araliphatic of 7-22 carbons or substituted or unsubstituted alicyclic of 5-12 carbons;
R⁴ and R⁵ are independently hydrogen, substituted or unsubstituted aliphatic of 1-20 carbons, substituted or unsubstituted carbocyclic aryl of 6-14 carbons, substituted or unsubstituted carbocyclic araliphatic of 7-22 carbons or substituted or unsubstituted alicyclic of 5-12 carbons which may optionally contain —N(R¹⁰)— as a ring member with the proviso that bonding to the amide nitrogen to which R⁴ and R⁵ are attached is through a carbon atom, or R⁴ and R⁵ may be linked together through —N(R¹⁰)— or —O— to form a heterocyclic ring including the nitrogen atom to which they are attached of 5-7 atoms with the proviso that the —N(R¹⁰)— or —O— linking R⁴ and R⁵ must be separated from the nitrogen atom to which R⁴ and R⁵ are attached by at least one carbon atom;
R⁶ is substituted or unsubstituted aliphatic of 1-20 carbons, substituted or unsubstituted alicyclic of 5-12 carbons, substituted or unsubstituted carbocyclic aryl of 6-14 carbons or substituted or unsubstituted carbocyclic araliphatic of 7-22 carbons,
R⁷, R⁸ and R⁹ are independently hydrogen, substituted or unsubstituted aliphatic of 1-20 carbons, substituted or unsubstituted alicyclic of 5-12 carbons, substituted or unsubstituted carbocyclic aryl of 6-14 carbons or substituted or unsubstituted carbocyclic araliphatic of 7-22 carbons, $R^{10}$ is hydrogen, substituted or unsubstituted aliphatic of 1-20 carbons, substituted or unsubstituted alicyclic of 5-12 carbons, substituted or unsubstituted carbocyclic araliphatic of 7-22 carbons, substituted or unsubstituted aliphatic acyl of 2-20 carbons, substituted or unsubstituted alicyclic acyl of 7-16 carbons, substituted or unsubstituted carbocyclic aromatic acyl of 7-11 carbons, substituted or unsubstituted carbocyclic araliphatic acyl of 7-22 carbons, —(C(=O))$_a$—N($R^4$)($R^5$), —(C(=O))$_a$—O—$R^6$, —(CH$_2$)$_a$—C(=O)—O—$R^7$ where a is 1-2, or —(CH$_2$—CH($R^8$)—O)$_b$—$R^9$ where b is 2-50, X is a triradical

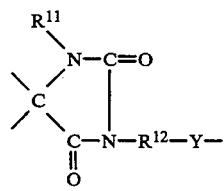

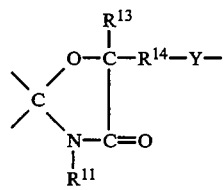

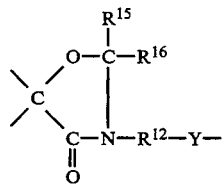

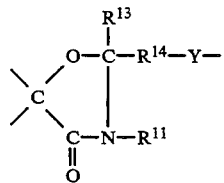

or

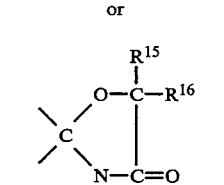

$R^{11}$ is independently of the same definition as $R^7$ and when alicyclic may optionally contain —N($R^{10}$)— as a ring member, with the proviso that bonding to the nitrogen atom to which "R" is attached must be through a carbon atom;

$R^{12}$ is substituted or unsubstituted aliphatic diradical of 1-20 carbons, substituted or unsubstituted carbocyclic aryl diradical of 6-12 carbons, substituted or unsubstituted alicyclic diradical of 5-12 carbons or substituted and unsubstituted carbocyclic araliphatic diradical of 7-22 carbons and the diradicals may optionally contain 1-6 heteroatoms —O—, —S—, and —N($R^{10}$)— with the proviso that multiple heteroatoms must be separated from each other by at least two carbon atoms and from the diradical ends by at least one carbon atom;

$R^{13}$ is independently of the same definition as $R^6$;

$R^{14}$ is independently of the same definition as $R^{12}$, and when Y is a direct bond, $R^{14}$ may also be a direct bond;

$R^{13}$ and $R^{14}$ together with the carbon atom linking them may form a substituted or unsubstituted cycloalkyl ring of 5-12 carbons, $R^{15}$ and $R^{16}$ are independently of the same definition as $R^{11}$ and may also be carbamoyl, alkoxycarbonyl of 2-5 carbons or pyridyl, and $R^{15}$ and $R^{16}$ may be linked together to form an alicyclic of 5-12 carbons, or may be linked together through a heteroatom —O—, —S—, and —N($R^{10}$)— to form a heterocyclic ring including the carbon atom to which they are attached of 5-7 atoms with the proviso that multiple heteroatoms must be separated from each other by at least two carbon atoms;

Y is —O—, —N($R^{11}$)— or a direct bond;

n is 1 or 2;

when n is 1, Z is

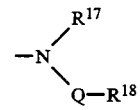

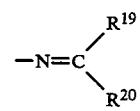

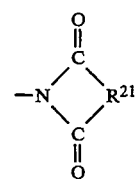

or

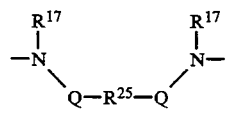

when n is 2, Z is

-N($R^{17}$)—Q—$R^{25}$—Q—N($R^{17}$)-

$R^{17}$ is independently of the same definition as $R^{11}$, $R^{18}$ is independently of the same definition as $R^{11}$, Q is —C(=O)—, —S(=O)$_2$—, —C(=O)—O—, —[C(=O)]$_2$—O—, —C(=O)—N($R^{10}$)—, —[C(=O)]$_2$—N($R^{10}$)—, —C(=S)—N($R^{10}$)—, —C(=O)—$R^{22}$—C(=O)—N($R^{10}$)— or, when n is 1, a direct bond between the nitrogen and $R^{18}$, $R^{19}$ and $R^{20}$ are independently of the same definition as $R^{11}$, and $R^{19}$ and $R^{20}$ may be linked together to form a substituted or unsubstituted alicyclic ring of 5-12 carbons or may be linked together through a heteroatom —N($R^{10}$)—, —O— and —S— to form a heterocyclic ring including the carbon atom to which they are attached of 5-12 atoms, $R^{21}$ is substituted or unsubstituted aliphatic diradical of 2-200 carbons, substituted or unsubstituted carbocyclic aryl diradical of 6-14 carbons, substituted or unsubstituted alicyclic diradical of 5-12 carbons or substituted or unsubstituted carbocyclic araliphatic diradical of 7-22 carbons, and the diradical chain(s) may optionally contain 1-6 heteroatoms —O—, —S— and —N($R^{10}$)— with the provisos that (a) multiple heteroatoms must be separated from each other by at least two carbon atoms and from the chain ends by at least one carbon atom, and that (b) the cyclic group formed contains 5-6 atoms in the ring, $R^{22}$ is a direct bond or is a substituted or unsubstituted aliphatic diradical of 1-200 carbons, substituted or unsubstituted carbocyclic aryl diradical of 6-14 carbons, substituted or unsubstituted alicyclic diradical of 5-12 carbons or substituted or unsubstituted carbocyclic araliphatic diradical of 7-22 carbons, and the diradical chain(s) may optionally contain 1-6 heteroatoms —O—, —S—, and —N($R^{10}$)— with the proviso that multiple heteroatoms must be separated from each other by at least two carbon atoms and from the chain ends by at least one carbon atom, $R^{23}$ is independently of the same definition as $R^{11}$, $R^{24}$ is chosen from —NH($R^{18}$), —OH and O$^-$M$^+$, where M$^+$ is sodium ion, potassium ion or ammonium ion, $R^{25}$ is substituted or unsubstituted aliphatic diradical of 1-20 carbons, substituted or unsubstituted aryl diradical of 6-12 carbons, substituted or unsubstituted alicyclic diradical of 5-12 carbons or substituted or unsubstituted carbocyclic araliphatic diradical of 7-22 carbons, and the diradical chain(s) may optionally contain 1-6 heteroatoms selected from —O— and —N($R^{10}$)— with the proviso that multiple heteroatoms must be separated from each other by at least two carbon atoms and from the chain ends by at least one carbon atom, and optional substitutents for $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{25}$ are one or more of the following: chloro, bromo, alkyl of 1-8 carbons, alkoxy of 1-12 carbons, phenoxy, cyano, hydroxy, epoxy, carboxy, benzoyl, benzoyloxy, dialkylamino of 2-8 carbons total, alkyoxycarbonyl of 2-6 carbons, acyloxy of 1-4 carbons, acryloyl, acryloyloxy, methacryloyl, methacryloyloxy, hydroxymethyl, hydroxyethyl, alkylthio of 1-4 carbons and trialkoxysilyl of 3-12 carbons; and additional optional substituents for $R^{21}$ and $R^{22}$ are alkyl of 5-180 carbons, alkylthio of 5-180 carbons, carbocyclic aralkylthio of 7-20 carbons, carbocyclic arylthio of 6-20 carbons, alkenyl of 2-180 carbons, cycloalkenyl of 5-12 carbons, carbocyclic aryl of 6-16 carbons, carbocyclic aralkyl of 7-17 carbons, carbocyclic aryloxy of 6-16 carbons, alkoxycarbonyl of 7-10 carbons, and (alkoxycarbonyl)alkylthio of 3-30 carbons; and additional substituents for $R^{18}$ are chosen from aliphatic of 1-20 carbons, cycloaliphatic of 5-12 carbons, carbocyclic aryl of 6-14 carbons, carbocyclic aralkyl of 7-22 carbons, alkoxy of 1-20 carbons, cycloalkoxy of 5-12 carbons, carbocyclic aryloxy of 6-14 carbons, carbocyclic aralkoxy of 7-15 carbons, aliphatic acyloxy of 2-20 carbons, alicyclic acyloxy of 6-13 carbons, carbocyclic aromatic acyloxy of 7-15 carbons, and carbocyclic araliphatic acyloxy of 8-16 carbons.

15. A stabilized composition in claim 14 wherein in the hindered amine compound:

$R^1$ is hydrogen, substituted or unsubstituted aliphatic of 1-4 carbons, substituted or unsubstituted carbocyclic araliphatic of 7-10 carbons, substituted or unsubstituted aliphatic acyl of 2-6 carbons or substituted or unsubstituted benzoyl, $R^2$ is hydrogen or methyl, $R^3$ is hydrogen, $R^4$ and $R^5$ are independently hydrogen, substituted or unsubstituted aliphatic of 1-8 carbons, substituted or unsubstituted phenyl or substituted or unsubstituted benzyl, $R^6$ is substituted or unsubstituted aliphatic of 1-8 carbons, substituted or unsubstituted phenyl or substituted or unsubstituted benzyl, $R^7$, $R^8$ and $R^9$ are independently hydrogen, substituted or unsubstituted aliphatic of 1-8 carbons, substituted or unsubstituted phenyl or substituted or unsubstituted benzyl, $R^{10}$ is hydrogen, substituted or unsubstituted aliphatic of 1-4 carbons, substituted or unsubstituted carbocyclic araliphatic of 7-10 carbons, substituted or unsubstituted aliphatic acyl of 2-6 carbons or substituted or unsubstituted benzoyl, $R^{15}$ and $R^{16}$ are independently substituted or unsubstituted aliphatic of 1-20 carbons, substituted or unsubstituted alicyclic of 5-6 carbons, substituted or unsubstituted carbocyclic aryl of 6-10 carbons, substituted or unsubstituted carbocyclic araliphatic of 7-16 carbons, or may be linked together to form an alicyclic of 5-12 carbons or may be linked together to form a group of formula

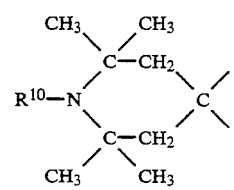

$R^{18}$ is selected from hydrogen, substituted or unsubstituted aliphatic of 1-12 carbons, substituted or unsubstituted alicyclic of 5-8 carbons, substituted or unsubstituted phenyl or substituted or unsubstituted carbocyclic araliphatic of 7-9 carbons and when alicyclic $R^{18}$ may optionally contain 1-2 heteroatoms selected from —O— and —N($R^{10}$)— with the proviso stated in claim 1, Q is —C(=O)—, —C(=O)—O—, —[C(=O)]-2—O—, —C(=O)—N($R^{10}$)—, —[C(=O)]-2—N($R^{10}$)— or, when n is 1, a direct bond between the nitrogen and $R^{18}$, $R^{19}$ and $R^{20}$ are independently substituted or unsubstituted aliphatic of 1-8 carbons, substituted or unsubstituted alicyclic of 5-8 carbons, substituted or unsubstituted carbocyclic aryl of 6-12 carbons or substituted or unsubstituted carbocyclic araliphatic of 7-14 carbons, and $R^{19}$ and $R^{20}$ may be linked together to form a substituted or unsubstituted cycloalkyl ring of 5-8 carbons or a group of formula

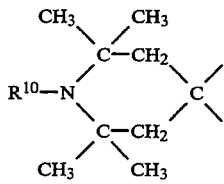

R$^{21}$ is substituted or unsubstituted aliphatic diradical of 2-18 carbons, substituted or unsubstituted orthophenylene or substituted or unsubstituted alicyclic diradical of 6-8 carbons, and the diradical chain(s) may optionally contain 1-2 heteroatoms —O— and —N(R$^{10}$)— with the proviso stated in claim 14, R$^{22}$ is substituted or unsubstituted aliphatic diradical of 2-18 carbons, substituted or unsubstituted phenylene or substituted or unsubstituted alicyclic diradical of 6-8 carbons, and the diradical chain(s) may optionally contain 1-2 heteroatoms —O— and —N(R$^{10}$)— with the proviso stated in claim 14, R$^{24}$ is —OH or —O$^-$M$^+$ where M is sodium ion, R$^{25}$ is substituted or unsubstituted aliphatic diradical of 2-12 carbons, substituted or unsubstituted aryl diradical of 6-12 carbons, substituted or unsubstituted alicyclic diradical of 5-12 carbons or substituted or unsubstituted araliphatic diradical of 7-12 carbons, and the diradical chain(s) may optionally contain 1-2 heteroatoms selected from —O— and —N(R$^{10}$)— with the proviso stated in claim 14.

16. A stabilized composition as defined in claim 15 wherein in the hindered amine compound:
R$^1$ is hydrogen, methyl, acetyl or benzoyl,
R$^2$ is hydrogen,
R$^4$ is hydrogen, methyl or ethyl,
R$^5$ is substituted or unsubstituted aliphatic of 1-8 carbons, or substituted or unsubstituted phenyl,
R$^{10}$ is hydrogen, methyl, acetyl or benzoyl,
R$^{17}$ is hydrogen, substituted or unsubstituted aliphatic of 1-10 carbons, substituted or unsubstituted cyclohexyl, substituted or unsubstituted phenyl or substituted or unsubstituted carbocyclic araliphatic of 7-14 carbons,
R$^{18}$ is selected from hydrogen, substituted or unsubstituted aliphatic of 1-10 carbons, substituted or unsubstituted cyclohexyl, substituted or unsubstituted phenyl or substituted or unsubstituted carbocyclic araliphatic of 7-14 carbons and when alicyclic R$^{18}$ may be substituted piperidin-4-yl,
R$^{24}$ is —OH,
R$^{25}$ is substituted or unsubstituted aliphatic diradical of 2-10 carbons, substituted or unsubstituted phenylene, substituted or unsubstituted alicyclic diradical of 5-8 carbons or substituted or unsubstituted carbocyclic araliphatic diradical of 7-12 carbons.

17. A stabilized composition as defined in claim 15 wherein in the hindered amine compound: R$^{17}$ is hydrogen, substituted or unsubstituted aliphatic of 1-12 carbons, substituted or unsubstituted alicyclic of 5-8 carbons, substituted or unsubstituted phenyl, or substituted or unsubstituted carbocyclic araliphatic of 7-9 carbons.

18. A stabilized composition as defined in claim 16 wherein the hindered amine compound is:
20-(3-hydrazino-3-oxopropyl)-2,2,4,4-tetramethyl-7-oxa-3,20,diaza-dispiro[5.1.11.2]heneicosane-21-one.

19. A stabilized composition as defined in claim 16 wherein the hindered amine compound is:
20-[5-(2,2,6,6-tetramethylpiperidine-4ylidene)-4,5-diaza-3-oxopentyl]-2,2,4,4-tetramethyl-7-oxa-3,20-diazadispiro[5.1.11.2]heneicosane-21-one.

20. A stabilized composition as defined in claim 14 wherein the hindered amine compound is:
20-[5-(3,3,5-trimethylcyclo-hexylidene)-4,5-diaza-3-oxopentyl]-2,2,4,4-tetramethyl-7-oxa-3,20-diazadispiro[5.1.11.2]heneicosane-21-one.

21. A stabilized composition as defined in claim 14 wherein the hindered amine compound is:
20-[4,5,7-triaza-3,6-dioxopentacosyl]-2,2,4,4-tetramethyl-7-oxa-3,20-diazadispiro[5.1.11.2]heneicosane-21-one.

22. A stabilized composition as defined in claim 16 wherein the hindered amine compound is 20-[8-(2,2,6,6-tetramethyl-4-piperidinyl)-4,5,8-triaza-3,6,7-trioxooctyl]-2,2,4,4-tetramethyl-7-oxa-3,20-diazadispiro[5.1.11.2]heneicosane-21-one.

23. A stabilized composition as defined in claim 16 wherein the hindered amine compound is:
20-(8-carboxy-4,5-diaza-3,6-dioxoheptacosyl)-2,2,4,4-tetramethyl-7-oxa-3,20-diazadispiro[5.1.11.2-]heneicosane-21-one.

24. A stabilized composition as defined in claim 16 wherein the hindered amine compound is:
20-{3-[N-(octadecylsuccinimido)amino]-3-oxopropyl}-2,2,4,4-tetramethyl-7-oxa-3,20-diazadispiro[5.1.11.2]heneicosane-21-one.

25. A stabilized composition as defined in claim 16 wherein the hindered amine compound is:
20-{3-[N-4-methyl-hexahydrophthalimido)amino]-3-oxopropyl}-2,2,4,4-tetramethyl-7-oxa-3,20-diazadispiro[5.1.11.2]heneicosane-21-one.

26. A stabilized composition as defined in claim 14 wherein the polymer is selected from the group polyolefins, ethylene-vinyl acetate copolymers, acrylic homopolymers, acrylic copolymers, styrene homopolymers, styrenic copolymers, styrenic polymer blends, polyphenylene ethers, polycarbonates, polyamides and mixtures thereof.

27. A stabilized composition as defined in claim 14 wherein the polymer is polypropylene.

28. A stabilized composition as defined in claim 14 having additionally incorporated therein 0.01 to 0.5% by weight of 2,4-di-t-butylphenyl-3,5-di-t-butyl-4-hydroxybenzoate.

29. A stabilized composition as defined in claim 27 having additionally incorporated therein 0.01 to 0.5% by weight of 2,4-di-t-butylphenyl-3,5-di-t-butyl-4-hydroxybenzoate.

* * * * *